United States Patent
Chou et al.

(10) Patent No.: US 10,870,618 B2
(45) Date of Patent: Dec. 22, 2020

(54) HISTONE DEACETYLASE INHIBITORS AND USES THEREOF

(71) Applicant: MUSC FOUNDATION FOR RESEARCH DEVELOPMENT, Charleston, SC (US)

(72) Inventors: Chung-Jen James Chou, Mt. Pleasant, SC (US); Jesse McClure, Charleston, SC (US); Cheng Zhang, Charleston, SC (US); Elizabeth Inks, Charleston, SC (US)

(73) Assignee: MUSC FOUNDATION FOR RESEARCH DEVELOPMENT, Charleston, SC (US)

( * ) Notice: Subject to any disclaimer, the term of this patent is extended or adjusted under 35 U.S.C. 154(b) by 0 days.

(21) Appl. No.: 16/340,458

(22) PCT Filed: Oct. 13, 2017

(86) PCT No.: PCT/US2017/056453
§ 371 (c)(1),
(2) Date: Apr. 9, 2019

(87) PCT Pub. No.: WO2018/071740
PCT Pub. Date: Apr. 19, 2018

(65) Prior Publication Data
US 2019/0308932 A1 Oct. 10, 2019

Related U.S. Application Data

(60) Provisional application No. 62/407,613, filed on Oct. 13, 2016.

(51) Int. Cl.
| | | |
|---|---|---|
| C07C 243/00 | (2006.01) | |
| C07C 243/38 | (2006.01) | |
| A61P 35/02 | (2006.01) | |
| C07C 243/26 | (2006.01) | |
| C07D 213/87 | (2006.01) | |
| C07D 307/68 | (2006.01) | |
| C07D 307/85 | (2006.01) | |
| C07D 333/38 | (2006.01) | |
| C07D 209/14 | (2006.01) | |
| C07C 243/32 | (2006.01) | |
| C07D 333/70 | (2006.01) | |

(52) U.S. Cl.
CPC ........... *C07C 243/38* (2013.01); *A61P 35/02* (2018.01); *C07C 243/00* (2013.01); *C07C 243/26* (2013.01); *C07C 243/32* (2013.01); *C07D 209/14* (2013.01); *C07D 213/87* (2013.01); *C07D 307/68* (2013.01); *C07D 307/85* (2013.01); *C07D 333/38* (2013.01); *C07D 333/70* (2013.01); *C07C 2603/02* (2017.05); *C07C 2603/04* (2017.05)

(58) Field of Classification Search
CPC .......................... C07C 243/00; C07C 243/38
See application file for complete search history.

(56) References Cited

U.S. PATENT DOCUMENTS

| | | | |
|---|---|---|---|
| 3,073,840 A | 1/1963 | Kano et al. | |
| 3,091,638 A * | 5/1963 | Gutmann | C07C 251/86 564/148 |
| 5,302,610 A | 4/1994 | Manning et al. | |
| 6,172,108 B1 | 1/2001 | Vega et al. | |
| 2010/0168101 A1 | 7/2010 | Bombrun et al. | |

FOREIGN PATENT DOCUMENTS

| | | | |
|---|---|---|---|
| GB | 865255 | * | 4/1961 |
| WO | 2015/073140 A1 | | 5/2015 |
| WO | 2015/153516 A1 | | 10/2015 |

OTHER PUBLICATIONS

PubChem CID 416453, National Center for Biotechnology Information. PubChem Database. N'-Methylbenzohydrazide, CID=416453, https://pubchem.ncbi.nlm.nih.gov/compound/416453 (accessed on Dec. 19, 2019), create date Mar. 26, 2005. (Year: 2005).*
Chemical Abstracts Registry No. 1039430-99-3, indexed in the Registry file on STN CAS Online Aug. 8, 2008. (Year: 2008).*
McClure et al., Journal of Medicinal Chemistry, Oct. 18, 2016, 59(21), pp. 9942-9959. (Year: 2016).*
Chemical Abstracts Registry No. 2044701-99-5, indexed in the Registry file on STN CAS Online Dec. 8, 2016. (Year: 2016).*
Chemical Abstracts Registry No. 1895422-06-6, indexed in the Registry file on STN CAS Online Apr. 22, 2016. (Year: 2016).*
Chemical Abstracts Registry No. 1314909-79-9, indexed in the Registry file on STN CAS Online Aug. 4, 2011. (Year: 2011).*
PubChem CID 19891826, National Center for Biotechnology Information. PubChem Database. CID=19891826, https://pubchem.ncbi.nlm.nih.gov/compound/N_-Ethyl-2-phenylacetohydrazide (accessed on May 25, 2020), create date Dec. 5, 2007. (Year: 2007).*
PubChem CID 69492182, National Center for Biotechnology Information. PubChem Database. CID=69492182, https://pubchem.ncbi.nlm.nih.gov/compound/N_-Ethyl-4-phenoxybenzohydrazide (accessed on May 25, 2020), create date Dec. 1, 2012. (Year: 2012).*
The International Search Report and Written Opinion, dated Dec. 29, 2017, in the corresponding PCT Patent Application No. PCT/US17/56453.

(Continued)

*Primary Examiner* — Laura L Stockton

(57) ABSTRACT

Provided herein are compounds of the formula (I) as well as pharmaceutically acceptable salts thereof, wherein the substituents are as those disclosed in the specification. These compounds, and the pharmaceutical compositions containing them, are useful for the treatment of cancer.

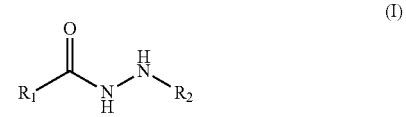

(I)

9 Claims, 12 Drawing Sheets

(56) References Cited

OTHER PUBLICATIONS

Vinsova et al. "Recent Advances on Isoniazide Derivatives", Anti-Infective Agents in Medicinal Chemistry, Jan. 1, 2008 (Jan. 1, 2008), vol. 7, pp. I2-31.
Gottesfeld et al. "Increasing frataxin gene expression with histone deacetylase inhibitors as a therapeutic approach for Friedreich's ataxia", Journal of Neurochemistry, Jul. 17, 2013 (Jul. 17, 2013), vol. 126, pp. 147-154.

* cited by examiner

HISTONE DEACETYLASE INHIBITORS AND USES THEREOF

CROSS-REFERENCE TO RELATED APPLICATIONS

This application is a National Stage Application of PCT/US2017/056453 filed on Oct. 13, 2017, which claims priority from U.S. Provisional Patent Application No. 62/407,613 filed on Oct. 13, 2016.

STATEMENT REGARDING FEDERALLY SPONSORED RESEARCH OR DEVELOPMENT

This invention was made with Government support under NIH grant R01 CA163452. The Government has certain rights in the invention.

FIELD OF THE INVENTION

The invention is directed to compounds of formula (I):

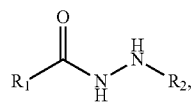

(I)

and to pharmaceutical compositions comprising the compounds. The compounds and compositions disclosed herein are histone deacetylase inhibitors useful for the treatment of cancer, such as, without limitation acute myeloid leukemia (AML), and inflammatory diseases and disorders.

All publications, patents, patent applications, and other references cited in this application are incorporated herein by reference in their entirety for all purposes and to the same extent as if each individual publication, patent, patent application or other reference was specifically and individually indicated to be incorporated by reference in its entirety for all purposes. Citation of a reference herein shall not be construed as an admission that such is prior art to the present invention.

BACKGROUND OF THE INVENTION

Histone deacetylases (HDACs) are regarded as highly attractive targets for cancer drug discovery. One of the biggest hurdles yet to be overcome for the continued improvement of HDAC inhibitors is finding alternative motifs equipotent to the classic and ubiquitously used hydroxamic acid. The N-hydroxyl group of this motif is highly subject to rapid sulfation/glucoronidation-based inactivation in humans. The compounds containing this motif, thus, require much higher dosing in the clinic to achieve therapeutic concentrations.

AML is characterized by the uncontrolled proliferation and survival of immature malignant myeloid cells in parallel with the concurrent loss of normal hematopoiesis. The lack of normal erythrocytes, platelets, and neutrophils causes a life-threatening deficiency that requires supportive care involving blood and platelet transfusions. Current standard anti-AML therapies are based on cytotoxic chemotherapy using antimetabolites such as cytarabine (ara-C), and one of the DNA intercalating anthracyclines such as daunorubicin or idarubicin. For younger patients (<60 years of age), this therapy achieves initial remission in 60-80% of patients; however, long-term survival (greater than 5 years) for this group still remains around 30%. For patients >60 years of age, which accounts for three-quarters of all AML patients, and patients who cannot tolerate the standard chemo-toxic treatments, the outcomes are far worse (median survival <3 months). Less than 10% of patients achieve disease-free survival greater than 5 years. With an increase in the life expectancy in the U.S., AML cases are expected to be more prevalent, and clearly there is a need for more effective and better-tolerated therapies.

Genetically, AML is a heterogeneous disease of the hematopoietic progenitor cells. Unlike chronic myelogenous leukemia, which is characterized by a more uniform genetic abnormality, a reciprocal translocation of the BCR and ABL genes, AML has various cytogenetic abnormalities and mutations. Studies have revealed several concurrent genetic abnormalities in a majority of AML patients: (1) Mutations within the FMS-like tyrosine kinase 3 (FLT3) gene on chromosome 13q12, which represents 25-35% of the patient population and is one of the most frequently identified genetic alterations in AML commonly associated with negative prognosis; (2) NPM1, a nuclear chaperone mutation, occurs in 25-35% of AML, which is usually associated with a positive clinical outcome; (3) mutated or over-expressed c-kit tyrosine kinase receptor, which represents 60-80% of patient population; (4) more than 12-27% of the patient population also has active Ras mutations. These constitutively active kinases initiate multiple pro-growth and pro-survival signaling through the mitogen-activated protein kinase/extracellular signal-regulated kinase (MAPK/Erk), Signal Transducer and Activator of Transcription 5 (STAT5), and PI3K/Akt kinase family mediated pathways similar to Bcr-Abl fusion protein in CML and confer poor prognosis in AML; and (5) multiple chromosomal translocations were also observed, which in most cases interact with a transcription co-repressor complex and alter gene expression required for myeloid development leading to leukemic transformation. These genetic aberrations are not mutually exclusive and commonly coexist in AML cells. Thus, the biggest challenge is to develop pharmacologic agents that contain significant specificity, yet are capable of attenuating multiple oncogenic signals in AML. The recent approval of midostaurin (Rydapt®) for newly diagnosed patients with mutant FLT3, indicates that a targeted approach for genetic-defined AML is a valid one.

HDACs control gene expression through histone deacetylation. Other than histone acetylation, HDACs also regulate various cellular signaling pathways through lysine post-translational modification. HDACs are involved in a wide range of biological responses such as apoptosis, autophagy, cellular differentiation, and immune-regulation. In addition, HDACs regulate non-histone protein function, localization, and stability; examples include p53, Hsp90, p65, and ULK1, and lysine post-translational modifications (PTMs) control their activity and localization. In the case of p53, acetylation modulates its activity and localization. Acetylation activates p53-dependent transcription, and in the cytosol, acetylated p53 can activate autophagy. For myeloid and lymphoid malignancies, class I HDACs play a crucial role in their transformation and survival. HDAC3 depletion or inhibition significantly reduces proliferation and promotes differentiation in leukemia. Inhibition or co-depletion of HDACs 1 and 2 elicits pro-apoptotic responses in leukemia. Furthermore, HDAC3 activity is required for the initiation of leukemogenesis in acute leukemia. From the preliminary data, the inhibition of class I HDACs 1, 2, and 3 induces lethal autophagy in AML and leads to the inhibition of multiple oncogenic and pro-survival pathways including FLT3/STAT5, p53, and HDAC6/tubulin which play a key role in Hsp90 and proteasome/lysosomal processes. These studies suggest that class I HDACs 1, 2, and 3 are potential molecular targets for the treatment of AML.

Chronic and severe inflammation is responsible for a variety of human disease from arthritis to inflammatory bowel diseases (IBDs). Current therapies of these chronic and severe inflammation diseases are usually ineffective and prone to treatment resistance including IBDs. Prevalence of IBDs such as ulcerative colitis and Crohn's disease is particularly high and affecting ~3.8 million people in North America and Europe, with an approximate economic burden of $30-45 billion dollars. The search for novel, effective, and safe, non-steroidal anti-inflammatory molecular targets and chemical entities has long been of great interest for the management of these chronic inflammatory diseases. The SCFA HDAC inhibitor butyrate and valproate are well known for their anti-inflammation properties, but highly potent hydroxamate HDAC inhibitors such as vorinostat and panobinostat have shown to induce pro-inflammatory and anti-inflammatory responses, depending on the system under investigation. HDAC inhibitor Trichostatin A has been shown to increase the duration of nuclear factor kappa-light-chain-enhancer of activated B cells (NF-κB) p65 nuclear localization and to prolong the duration of its pro-inflammatory signaling. Moreover, conflicting reports exist for HDAC3 and its roles in NF-κB regulation. Chen et al. reported that deacetylated p65 is required for its interaction with the nuclear factor of kappa light polypeptide gene enhancer in B-cells inhibitor alpha (IκBa) for its nuclear export, while Kiernan et al. indicates that acetylation of p65 is required for its interaction with IκBa and promoter dissociation. Several other studies have shown that inhibition of HDAC extends NF-κB activation. Vorinostat has been shown to also decrease NF-κB activation and prevent p65 accumulation in immune responses. More detailed studies have shown that only low concentrations of vorinostat are anti-inflammatory, while the class I HDAC-selective amino-benzamide HDAC inhibitor's anti-inflammatory effect is only significant at high concentration. These data indicate that perhaps different HDAC isozymes play opposite roles in inflammation signaling. Genetics approaches have also displayed this HDAC paradox in immune regulation. Class I HDACs, mainly HDACs 1, 2, and 3, have been shown to play both positive and negative regulatory roles in the complex immuno-regulatory system. In particular, decreases in HDACs 1, 2, and 3 activity have been associated with exacerbation of symptoms in several inflammatory disease models. Further, genetic silencing of class I HDACs has also indicated that their deacetylation activity appears to play a role in immuno-activation and pro-inflammatory responses.

The major limitations of all current HDAC inhibitors include limited HDAC isozyme selectivity, poor in vivo pharmacokinetic profiles, and long-term safety concerns due to the potential mutagenicity associated with their key metal-binding motif. All these factors limit the current HDAC inhibitors' usefulness in elucidating the HDAC anti-inflammatory mechanism and as potential agents for use as NSAIDs long-term.

There is a need, therefore, for the development of new HDAC inhibitors that lack the non-specific hydroxamic acid metal chelating group in the art, while possessing minimal toxicity and improved pharmacokinetic profiles.

SUMMARY OF THE INVENTION

The present invention is directed to compounds according to formula (I):

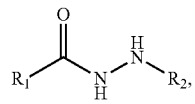

wherein:

$R_1$ is—a monocyclic or bicyclic aryl group or a monocyclic or bicyclic heteroaryl group, said aryl and heteroaryl groups optionally substituted independently with alkoxy, O-phenyl, phenyl, —CH$_2$NHC(O)-phenyl, —CH$_2$NHC(O)C=C-phenyl or —CH=CH-phenyl-CH$_2$NHCH$_2$CH$_2$-1H-indol-3-yl-methyl; or a lower alkyl or alkenyl group, optionally substituted with phenyl; and $R_2$ is an alkyl or alkenyl group, optionally substituted with —CF$_3$ or cycloalkyl, or a pharmaceutically acceptable salt thereof.

The present invention is also directed to pharmaceutical compositions containing the compounds of formula (I) and to methods of using these compounds.

DETAILED DESCRIPTION OF THE INVENTION

Figure 1:
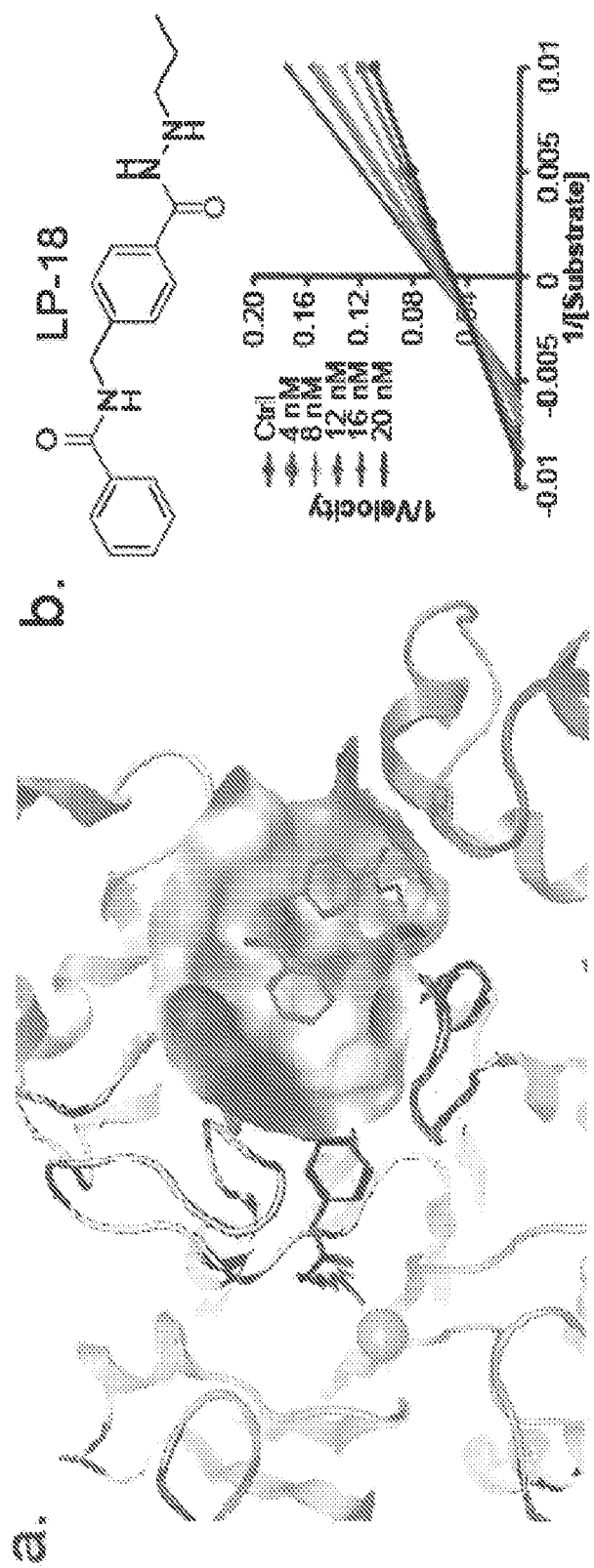
FIG. 1 shows a) allosteric HDAC inhibitor (LP-18; green) is predicted to bind near the interface of HDAC3 (gray) and its co-repressor NCoR (gold). Vorinostat (suberanilohydroxamic acid; black), a competitive HDAC inhibitor, is interacting with the zinc ion. b. The structure of LP-18 and its mixed inhibition Lineweaver-Burke plot indicate an allosteric inhibition mechanism (HDAC3 shown).

Provided herein are potent HDAC inhibitors having a hydrazide motif. The inhibitors are distinguishable from the FDA approved HDAC inhibitors which contain hydroxamic acid motifs. The hydroxamic acid motif is a promiscuous metal chelator group that leads to off-target, non-HDAC binding site metal chelation. Further, this group, as well as another commonly used metal chelating group, ortho-aminoanilide, is extensively inactivated via glucuronidation in vivo in addition to being hepatotoxic. The inhibitors of the invention, by contrast, show higher potency than the FDA approved agents having non-specific hydroxamic acid metal chelating group, while simultaneously demonstrating lower toxicity in vivo. The compounds of the invention also advantageously possess, for example, low nanomolar activity against models of AML and are at least 100-fold more selective for AML than solid tumor cells such as Hek293 or human peripheral blood mononuclear cells.

It is to be understood that the terminology employed herein is for the purpose of describing particular embodiments, and is not intended to be limiting. Further, although any methods, devices and materials similar or equivalent to those described herein can be used in the practice or testing of the invention, certain embodiments of such methods, devices and materials are now described As used herein, the term "alkenyl", alone or in combination with other groups, refers to a straight-chain or branched hydrocarbon residue having an olefinic bond.

As used herein, the term "alkyl", alone or in combination with other groups, refers to a branched or straight-chain monovalent saturated aliphatic hydrocarbon radical of one to twenty carbon atoms, in one embodiment one to sixteen carbon atoms, in another embodiment one to ten carbon atoms.

The term "lower alkyl", alone or in combination with other groups, refers to a branched or straight-chain alkyl radical of one to nine carbon atoms, in one embodiment one to six carbon atoms, in another embodiment one to four carbon atoms. This term is further exemplified by radicals such as methyl, ethyl, n-propyl, isopropyl, n-butyl, s-butyl, isobutyl, t-butyl, n-pentyl, 3-methylbutyl, n-hexyl, 2-ethylbutyl and the like.

As used herein, the term "alkoxy" means alkyl-O—; and "alkoyl" means alkyl-CO—. Alkoxy substituent groups or alkoxy-containing substituent groups may be substituted by, for example, one or more alkyl or halo groups.

As used herein, the term "halogen" means a fluorine, chlorine, bromine or iodine radical, preferably a fluorine, chlorine or bromine radical, and more preferably a fluorine, bromine or chlorine radical.

The term "aryl" refers to an aromatic mono- or polycarbocyclic (e.g., bicyclic) radical of 6 to 12 carbon atoms having at least one aromatic ring. Examples of such groups include, but are not limited to, phenyl, naphthyl, 1,2,3,4-tetrahydronaphthalene, 1,2-dihydronaphthalene, indanyl, 1H-indenyl and the like.

The term "heteroaryl," refers to an aromatic mono- or polycyclic (e.g., bicyclic) radical of 5 to 12 atoms having at least one aromatic ring containing one, two, or three ring heteroatoms selected from N, O, and S, with the remaining ring atoms being C. One or two ring carbon atoms of the heteroaryl group may be replaced with a carbonyl group.

The term "cycloalkyl" refers to a monovalent mono- or polycarbocyclic radical of three to ten, preferably three to six carbon atoms. This term is further exemplified by radicals such as cyclopropyl, cyclobutyl, cyclopentyl, cyclohexyl, cycloheptyl, norbornyl, adamantyl, indanyl and the like. In a preferred embodiment, the "cycloalkyl" moieties can optionally be substituted with one, two, three or four substituents. Each substituent can independently be, alkyl, alkoxy, halogen, amino, hydroxyl or oxygen unless otherwise specifically indicated. Examples of cycloalkyl moieties include, but are not limited to, optionally substituted cyclopropyl, optionally substituted cyclobutyl, optionally substituted cyclopentyl, optionally substituted cyclopentenyl, optionally substituted cyclohexyl, optionally substituted cyclohexylene, optionally substituted cycloheptyl, and the like or those which are specifically exemplified herein.

The term "heterocycloalkyl" denotes a mono- or polycyclic (e.g., bicyclic) alkyl ring, wherein one, two or three of the carbon ring atoms is replaced by a heteroatom such as N, O or S. Examples of heterocycloalkyl groups include, but are not limited to, morpholinyl, thiomorpholinyl, piperazinyl, piperidinyl, pyrrolidinyl, tetrahydropyranyl, tetrahydrofuranyl, 1,3-dioxanyl and the like. The heterocycloalkyl groups may be unsubstituted or substituted and attachment may be through their carbon frame or through their heteroatom(s) where appropriate.

The alkyl, lower alkyl, aryl and heteroaryl groups may be substituted or unsubstituted. When substituted, there will generally be, for example, 1 to 4 substituents present. These substituents may optionally form a ring with the alkyl, lower alkyl or aryl group with which they are connected. Substituents may include, for example: carbon-containing groups such as alkyl, aryl, arylalkyl (e.g. substituted and unsubstituted phenyl, substituted and unsubstituted benzyl); halogen atoms and halogen-containing groups such as haloalkyl (e.g. trifluoromethyl); oxygen-containing groups such as alcohols (e.g. hydroxyl, hydroxyalkyl, aryl(hydroxyl)alkyl), ethers (e.g. alkoxy, aryloxy, alkoxyalkyl, aryloxyalkyl, in one embodiment, for example, methoxy and ethoxy), aldehydes (e.g. carboxaldehyde), ketones (e.g. alkylcarbonyl, alkylcarbonylalkyl, arylcarbonyl, arylalkylcarbonyl, arycarbonylalkyl), acids (e.g. carboxy, carboxyalkyl), acid derivatives such as esters (e.g. alkoxycarbonyl, alkoxycarbonylalkyl, alkylcarbonyloxy, alkylcarbonyloxyalkyl), amides (e.g. aminocarbonyl, mono- or di-alkylaminocarbonyl, aminocarbonylalkyl, mono- or di-alkylaminocarbonylalkyl, arylaminocarbonyl), carbamates (e.g. alkoxycarbonylamino, aryloxycarbonylamino, aminocarbonyloxy, mono- or di-alkylaminocarbonyloxy, arylminocarbonloxy) and ureas (e.g. mono- or di-alkylaminocarbonylamino or arylaminocarbonylamino); nitrogen-containing groups such as amines (e.g. amino, mono- or di-alkylamino, aminoalkyl, mono- or di-alkylaminoalkyl), azides, nitriles (e.g. cyano, cyanoalkyl), nitro; sulfur-containing groups such as thiols, thioethers, sulfoxides and sulfones (e.g. alkylthio, alkylsulfinyl, alkylsulfonyl, alkylthioalkyl, alkylsulfinylalkyl, alkylsulfonylalkyl, arylthio, arysulfinyl, arysulfonyl, arythioalkyl, arylsulfinylalkyl, arylsulfonylalkyl); and heterocyclic groups containing one or more heteroatoms, (e.g. thienyl, furanyl, pyrrolyl, imidazolyl, pyrazolyl, thiazolyl, isothiazolyl, oxazolyl, oxadiazolyl, thiadiazolyl, aziridinyl, azetidinyl, pyrrolidinyl, pyrrolinyl, imidazolidinyl, imidazolinyl, pyrazolidinyl, tetrahydrofuranyl, pyranyl, pyronyl, pyridyl, pyrazinyl, pyridazinyl, piperidyl, hexahydroazepinyl, piperazinyl, morpholinyl, thianaphthyl, benzofuranyl, isobenzofuranyl, indolyl, oxyindolyl, isoindolyl, indazolyl, indolinyl, 7-azaindolyl, benzopyranyl, coumarinyl, isocoumarinyl, quinolinyl, isoquinolinyl, naphthridinyl, cinnolinyl, quinazolinyl, pyridopyridyl, benzoxazinyl, quinoxalinyl, chromenyl, chromanyl, isochromanyl, phthalazinyl and carbolinyl).

Compounds of formula I can have one or more asymmetric carbon atoms and can exist in the form of optically pure enantiomers, mixtures of enantiomers such as, for example, racemates, optically pure diastereoisomers, mixtures of diastereoisomers, diastereoisomeric racemates or mixtures of diastereoisomeric racemates. The optically active forms can be obtained for example by resolution of the racemates, by asymmetric synthesis or asymmetric chromatography (chromatography with a chiral adsorbents or eluant). The invention embraces all of these forms.

As used herein, the term "pharmaceutically acceptable salt" means any pharmaceutically acceptable salt of the compound of formula (I). Salts may be prepared from pharmaceutically acceptable non-toxic acids and bases including inorganic and organic acids and bases. Such acids include, for example, acetic, benzenesulfonic, benzoic, camphorsulfonic, citric, ethenesulfonic, dichloroacetic, formic, fumaric, gluconic, glutamic, hippuric, hydrobromic, hydrochloric, isethionic, lactic, maleic, malic, mandelic, methanesulfonic, mucic, nitric, oxalic, pamoic, pantothenic, phosphoric, succinic, sulfuric, tartaric, oxalic, p-toluenesulfonic and the like. In certain embodiments, fumaric, hydrochloric, hydrobromic, phosphoric, succinic, sulfuric and methanesulfonic acids. Acceptable base salts include alkali metal (e.g. sodium, potassium), alkaline earth metal (e.g. calcium, magnesium) and aluminum salts.

In the practice of the method of the present invention, an effective amount of any one of the compounds of this invention or a combination of any of the compounds of this invention or a pharmaceutically acceptable salt thereof, is administered via any of the usual and acceptable methods known in the art, either singly or in combination. The compounds or compositions can thus be administered, for example, ocularly, orally (e.g., buccal cavity), sublingually, parenterally (e.g., intramuscularly, intravenously, or subcutaneously), rectally (e.g., by suppositories or washings), transdermally (e.g., skin electroporation) or by inhalation (e.g., by aerosol), and in the form or solid, liquid or gaseous dosages, including tablets and suspensions. The administration can be conducted in a single unit dosage form with continuous therapy or in a single dose therapy ad libitum. The therapeutic composition can also be in the form of an oil emulsion or dispersion in conjunction with a lipophilic salt such as pamoic acid, or in the form of a biodegradable sustained-release composition for subcutaneous or intramuscular administration.

Useful pharmaceutical carriers for the preparation of the compositions hereof, can be solids, liquids or gases. Thus, the compositions can take the form of tablets, pills, capsules, suppositories, powders, enterically coated or other protected formulations (e.g. binding on ion-exchange resins or packaging in lipid-protein vesicles), sustained release formulations, solutions, suspensions, elixirs, aerosols, and the like. The carrier can be selected from the various oils including those of petroleum, animal, vegetable or synthetic origin, e.g., peanut oil, soybean oil, mineral oil, sesame oil, and the like. Certain embodiments, water, saline, aqueous dextrose, and glycols are liquid carriers, particularly (when isotonic with the blood) for injectable solutions. For example, formulations for intravenous administration comprise sterile aqueous solutions of the active ingredient(s) which are prepared by dissolving solid active ingredient(s) in water to produce an aqueous solution, and rendering the solution sterile. Suitable pharmaceutical excipients include starch, cellulose, talc, glucose, lactose, talc, gelatin, malt, rice, flour, chalk, silica, magnesium stearate, sodium stearate, glycerol monostearate, sodium chloride, dried skim milk, glycerol, propylene glycol, water, ethanol, and the like. The compositions may be subjected to conventional pharmaceutical additives such as preservatives, stabilizing agents, wetting or emulsifying agents, salts for adjusting osmotic pressure, buffers and the like. Suitable pharmaceutical carriers and their formulation are described in Remington's Pharmaceutical Sciences by E. W. Martin. Such compositions will, in any event, contain an effective amount of the active compound together with a suitable carrier so as to prepare the proper dosage form for proper administration to the recipient.

The dose of a compound of the present invention depends on a number of factors such as, for example, the manner of administration, the age and the body weight of the subject, and the condition of the subject to be treated, and ultimately will be decided by the attending physician or veterinarian. Such an amount of the active compound as determined by the attending physician or veterinarian is referred to herein, and in the claims, as a "therapeutically effective amount". For example, the dose of a compound of the present invention is typically in the range of about 1 to about 1000 mg per day. In one embodiment, the therapeutically effective amount is in an amount of from about 1 mg to about 500 mg per day. In another embodiment, one to four doses can be given per day.

It will be appreciated, that the compounds of general formula I of this invention may be derivatized at functional groups to provide derivatives which are capable of conversion back to the parent compound in vivo. Physiologically acceptable and metabolically labile derivatives, which are capable of producing the parent compounds of general formula I in vivo are also within the scope of this invention.

Representative compounds of the invention made by the processes in the Schemes and Examples below include the following:

| Compound | Structure | IUPAC Name |
|---|---|---|
| 1a | 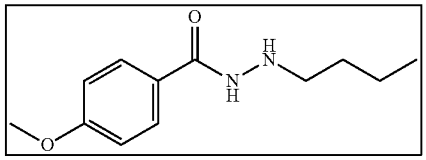 [SMILES: CCCCNNC(=O)c1ccc(OC)cc1] | N'-butyl-4-methoxybenzohydrazide |
| 1b | 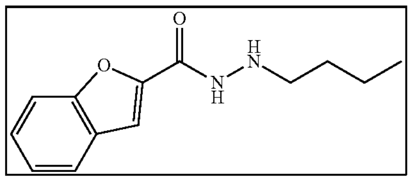 [SMILES: CCCCNNC(=O)c1cc2ccccc2o1] | N'-butylbenzofuran-2-carbohydrazide |
| 1c | 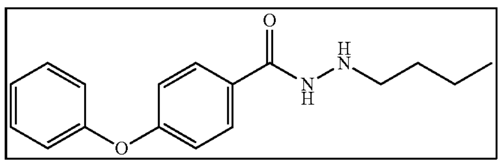 [SMILES: CCCCNNC(=O)c1ccc(Oc2ccccc2)cc1] | N'-butyl-4-phenoxybenzohydrazide |
| 1d | 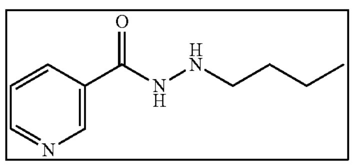 | N'-butylnicotinohydrazide |
| 1e | 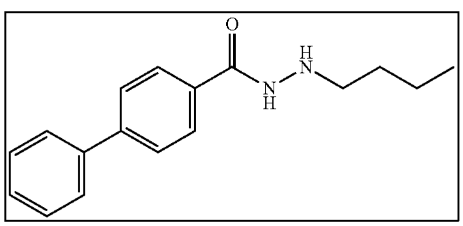 [SMILES: CCCCNNC(=O)c1ccc(-c2ccccc2)cc1] | N'-butyl-[1,1'-biphenyl]-4-carbohydrazide |
| 1f | 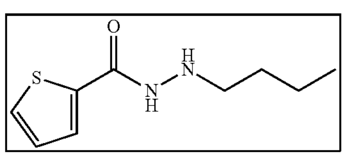 | N'-butylthiophene-2-carbohydrazide |
| 1g | 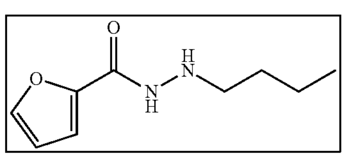 | N'-butylfuran-2-carbohydrazide |
| 1h | 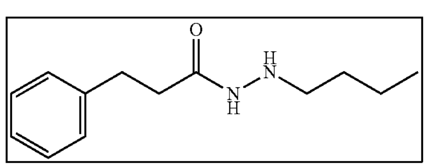 [SMILES: CCCCNNC(=O)CCc1ccccc1] | N'-butyl-3-phenylpropanehydrazide |

-continued

| Compound | Structure | IUPAC Name |
|---|---|---|
| 1i | 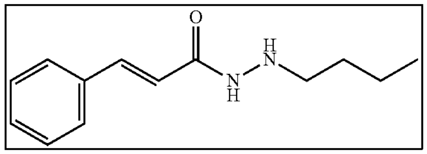 [SMILES: CCCCNNC(=O)/C=C/c1ccccc1] | N'-butylcinnamohydrazide |
| 1j | 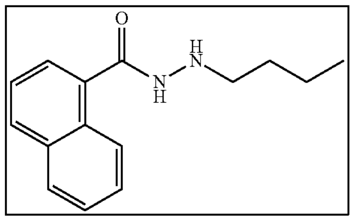 [SMILES: CCCCNNC(=O)c1cccc2ccccc12] | N'-butyl-1-naphthohydrazide |
| 1k | 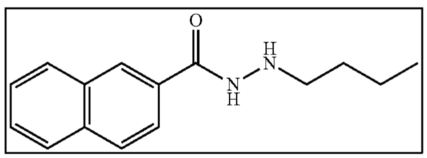 [SMILES: CCCCNNC(=O)c1ccc2ccccc2c1] | N'-butyl-2-naphthohydrazide |
| 1l | 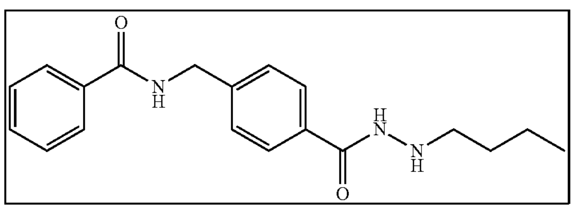 [SMILES: CCCCNNC(=O)c1ccc(CNC(=O)c2ccccc2)cc1] | N-(4-(2-butylhydrazine-1-carbonyl)benzyl)benzamide |
| 2a | 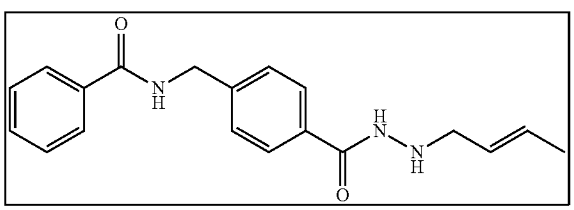 [SMILES: C/C=C/CNNC(=O)c1ccc(CNC(=O)c2ccccc2)cc1] | (E)-N-(4-(2-(but-2-en-1-yl)hydrazine-1-carbonyl)benzyl)benzamide |
| 2b | 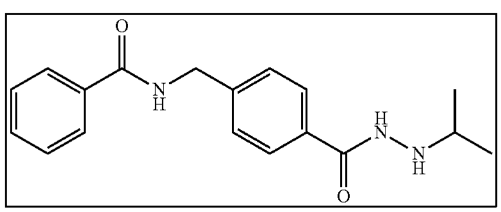 [SMILES: CC(C)NNC(=O)c1ccc(CNC(=O)c2ccccc2)cc1] | N-(4-(2-isopropylhydrazine-1-carbonyl)benzyl)benzamide |
| 2c | 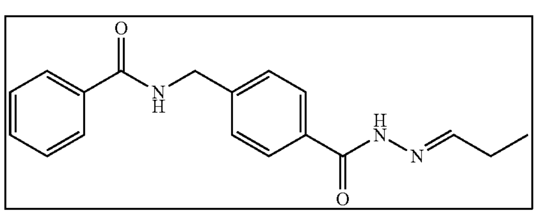 [SMILES: CC/C=N/NC(=O)c1ccc(CNC(=O)c2ccccc2)cc1] | (E)-N-(4-(2-propylidenehydrazine-1-carbonyl)benzyl)benzamide |

-continued

| Compound | Structure | IUPAC Name |
|---|---|---|
| 2d | 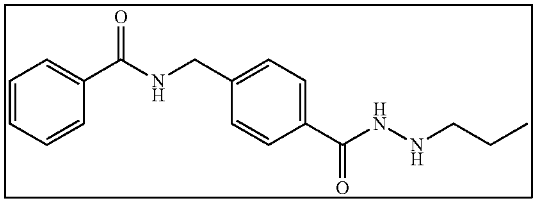 [SMILES: CCCNNC(=O)c1ccc(CNC(=O)c2ccccc2)cc1] | N-(4-(2-propylhydrazine-1-carbonyl)benzyl)benzamide |
| 2e | 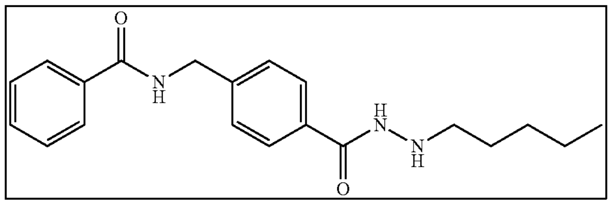 [SMILES: CCCCCNNC(=O)c1ccc(CNC(=O)c2ccccc2)cc1] | N-(4-(2-pentylhydrazine-1-carbonyl)benzyl)benzamide |
| 2f | 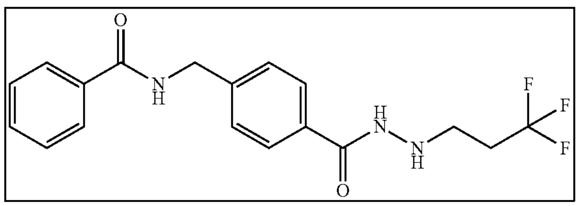 [SMILES: O=C(NCc1ccc(C(=O)NNCCC(F)(F)F)cc1)c1ccccc1] | N-(4-(2-(3,3,3-trifluoropropyl)hydrazine-1-carbonyl)benzyl)benzamide |
| 2g | 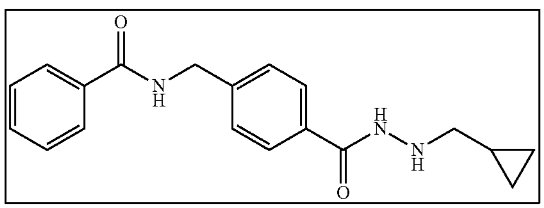 [SMILES: O=C(NCc1ccc(C(=O)NNCC2CC2)cc1)c1ccccc1] | N-(4-(2-(cyclopropylmethyl)hydrazine-1-carbonyl)benzyl)benzamide |
| 2h | 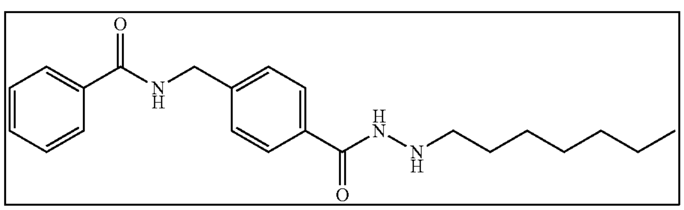 [SMILES: CCCCCCCNNC(=O)c1ccc(CNC(=O)c2ccccc2)cc1] | N-(4-(2-heptylhydrazine-1-carbonyl)benzyl)benzamide |
| 2i | 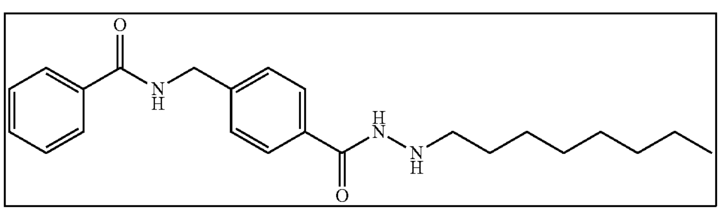 [SMILES: CCCCCCCCNNC(=O)c1ccc(CNC(=O)c2ccccc2)cc1] | N-(4-(2-octylhydrazine-1-carbonyl)benzyl)benzamide |
| 2j | 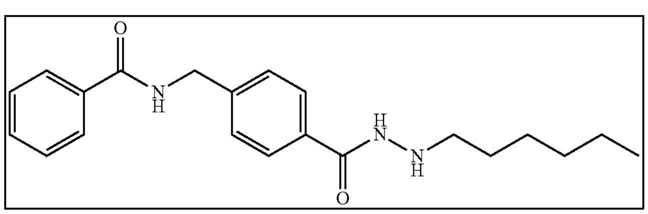 [SMILES: CCCCCCNNC(=O)c1ccc(CNC(=O)c2ccccc2)cc1] | N-(4-(2-hexylhydrazine-1-carbonyl)benzyl)benzamide |

-continued

| Compound | Structure | IUPAC Name |
|---|---|---|
| 2k | 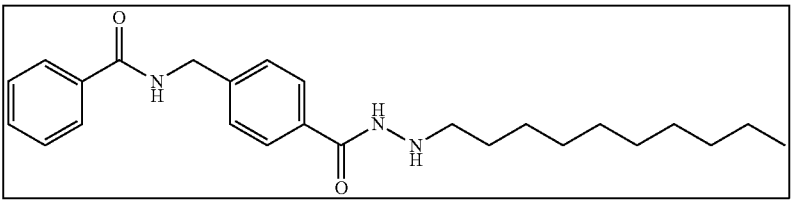 [SMILES: CCCCCCCCCCNNC(=O)c1ccc(CNC(=O)c2ccccc2)cc1] | N-(4-(2-decylhydrazine-1-carbonyl)benzyl)benzamide |
| 2l | 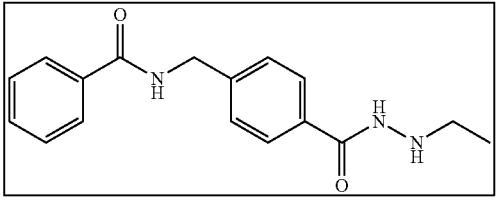 [SMILES: CCNNC(=O)c1ccc(CNC(=O)c2ccccc2)cc1] | N-(4-(2-ethylhydrazine-1-carbonyl)benzyl)benzamide |
| 2m | 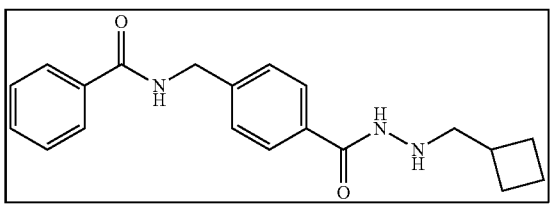 [SMILES: O=C(NCc1ccc(C(=O)NNCC2CCC2)cc1)c1ccccc1] | N-(4-(2-(cyclobutylmethyl)hydrazine-1-carbonyl)benzyl)benzamide |
| 3a | 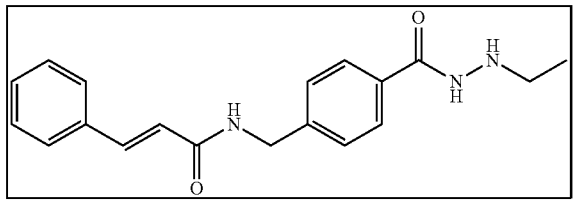 [SMILES: CCNNC(=O)c1ccc(CNC(=O)/C=C/c2ccccc2)cc1] | N-(4-(2-ethylhydrazine-1-carbonyl)benzyl)cinnamamide |
| 3b | 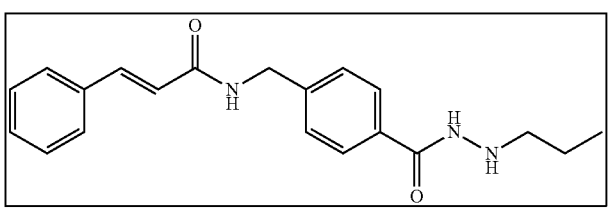 [SMILES: CCCNNC(=O)c1ccc(CNC(=O)/C=C/c2ccccc2)cc1] | N-(4-(2-propylhydrazine-1-carbonyl)benzyl)cinnamamide |
| 3c | 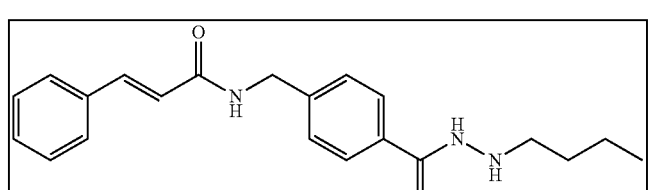 | N-(4-(2-butylhydrazine-1-carbonyl)benzyl)cinnamamide |
| 3d | 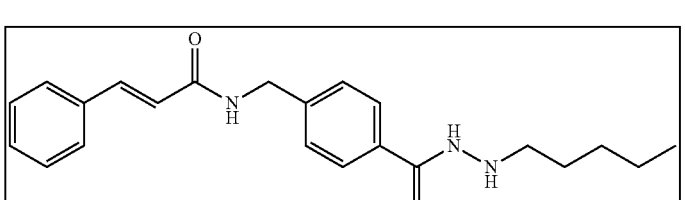 | N-(4-(2-pentylhydrazine-1-carbonyl)benzyl)cinnamamide |

| Compound | Structure | IUPAC Name |
|---|---|---|
| 3e | ![structure] | N-(4-(2-hexylhydrazine-1-carbonyl)benzyl)cinnamamide |

Compounds of the present invention can be prepared beginning with commercially available starting materials and utilizing general synthetic techniques and procedures known to those skilled in the art. For example, the compounds of formula I can be prepared according to the following scheme:

Scheme 1
Butylhydrazide Derivatives Synthesis[a]

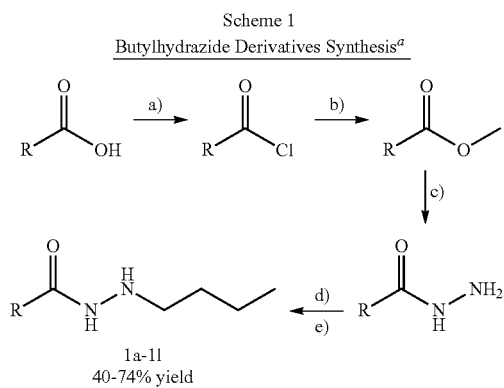

1a-1l
40-74% yield

[a]Reagents and conditions:
(a) methylene chloride, rt, oxalyl chloride, cat. DMF;
(b) MeOH, rt;
(c) MeOH, reflux, NH2NH2·H2O;
(d) EtOH, reflux, butaldehyde, MgSO4;
(e) MeOH, rt, NaBH3CN, conc. HCl As shown in Scheme 1, the corresponding hydrazide molecule through reactions a, b, and c, depending on the composition of the starting molecule can be generated. Target hydrazide compounds can be reacted with butylaldehyde to generate the compound of interest. Carboxylic acids can be reacted with oxalyl chloride in methylene chloride with catalytic amounts of dimethylformamide (Scheme 1, reaction a). The resulting acyl chloride, or commercially purchased acyl chlorides can be stirred in methanol to give the corresponding methyl ester (Scheme 1, reaction b). The generated or commercially purchased methyl esters can be refluxed in methanol with a hydrazine water salt to generate a hydrazide of interest (Scheme 1, reaction c). The resulting compounds can be then refluxed in ethanol in the presence of magnesium sulfate and butylaldehyde followed by a reduction with sodium cyanoborohydride in acidified methanol to give the desired products 1a-1l (Scheme 1, reactions d and e). A notable exception to this scheme can be the synthesis of 1d, which is unable to be esterified from the commercially available corresponding acyl chloride until the addition of two equivalents of triethylamine. Additionally, compound 1i spontaneously formed the corresponding pyrazolidinone when reacted with the hydrazine salt due to the presence of an unsaturated bond alpha to the ester carbonyl. Instead, the carboxylic acid starting material can be reacted with HoBT and DCC in acetonitrile. The resulting intermediate can be reacted with the hydrazine water salt in acetonitrile to yield the corresponding hydrazide. Lastly, compound 1l can be the result of reacting methyl 4-(aminomethyl)benzoate with benzoyl chloride to generate the methyl ester corresponding to 1l. From here, the reaction carried on as shown in Scheme 1, reactions d and e.

Scheme 2
N-(4-(hydrazide)benzyl)benzamide Derivatives Synthesis[a]

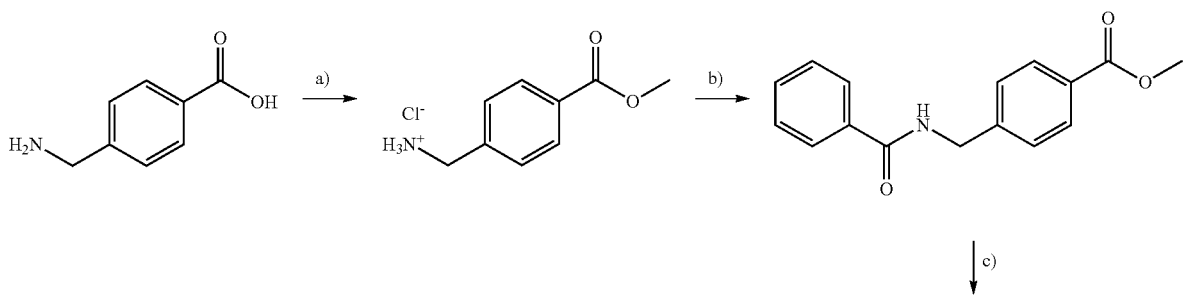

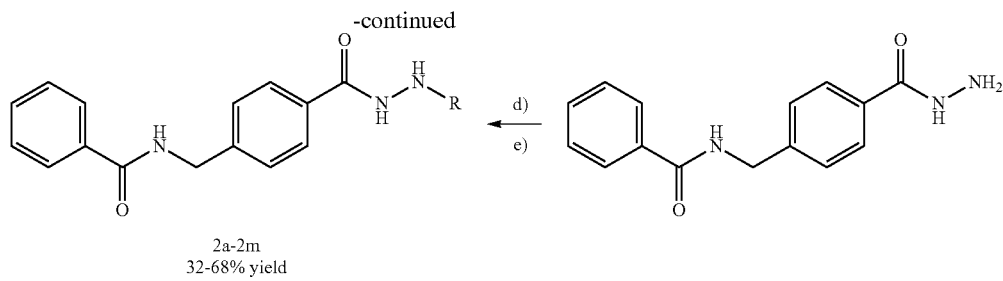

2a-2m
32-68% yield

<sup>a</sup>Reagents and conditions: (a) MeOH, reflux, conc. HCl; (b) AcOEt:H2O (1:1), rt, K2CO3; (c) MeOH, reflux, NH2NH2•H2O; (d) EtOH, rt, aldehyde of interest, MgSO4; (e) MeOH, NaBH3CN, conc. HCl As shown in Scheme 2, the starting material, 4-(aminomethyl)benzoic acid, can be refluxed in methanol and concentrated acid to generate the much more soluble corresponding methyl ester hydrochloride salt (Scheme 2, reaction a). This intermediate can be reacted with benzoyl chloride in ethyl acetate and water in the presence of potassium carbonate to form an amide bond and afford 4-(benzamidomethyl)benzoate (Scheme 2, reaction b). This can be (1:1), in turn, refluxed with the hydrazine water salt in methanol to generate the desired intermediate (Scheme 2, reaction c). Lastly, this intermediate can be N-methylated using various aldehydes in ethanol and magnesium sulfate followed by reduction using sodium cyanoborohydride in acidified methanol to yield the desired products, 2a-2m (Scheme 2, reactions d and e).

Scheme 3
N-(4-(hydrazide)benzyl)cinnamamide Derivatives Synthesis<sup>a</sup>

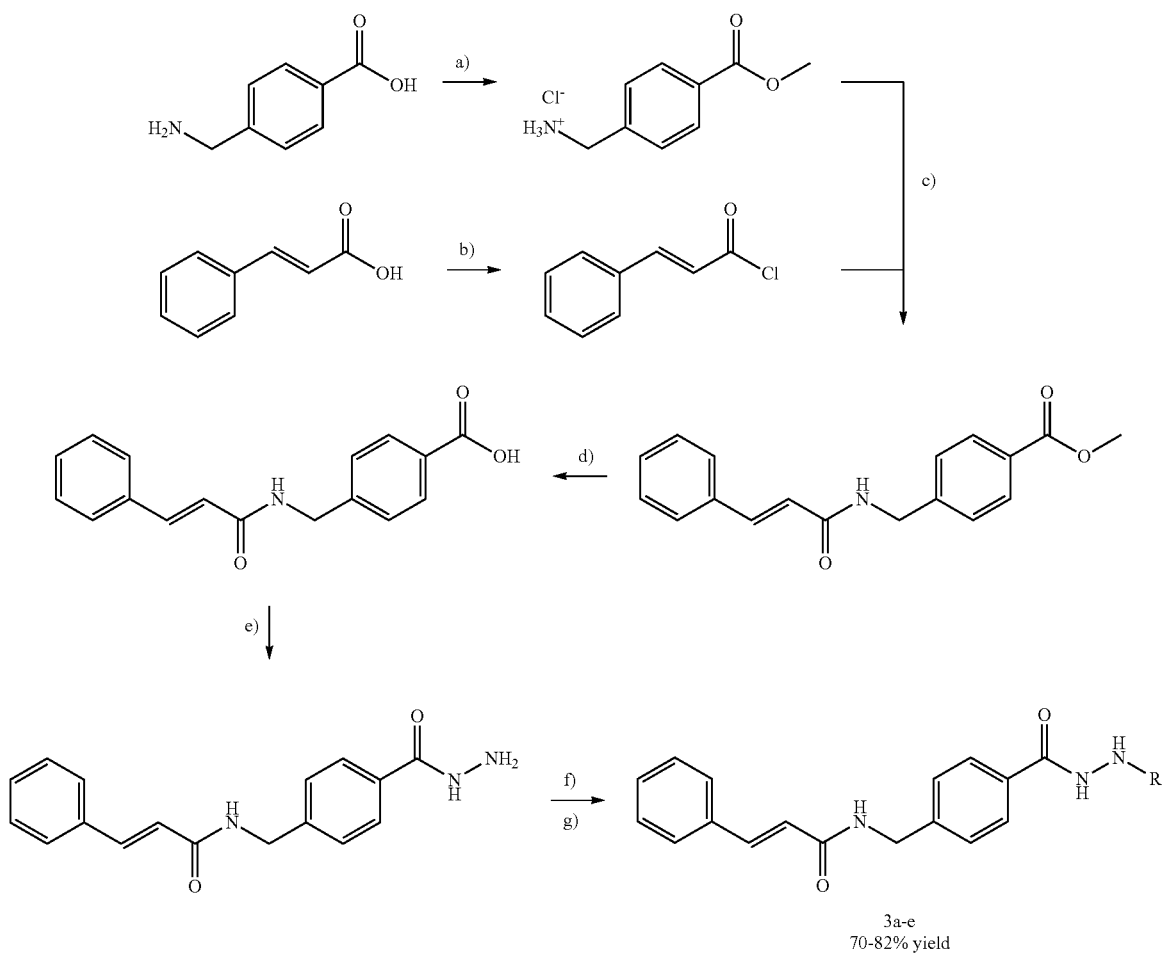

3a-e
70-82% yield

<sup>a</sup>Reagents and conditions: (a) MeOH, reflux, conc. HCl; (b) DCM, rt, Oxalyl Chloride, cat. DMF; (c) EtOAc:H2O (1:1), rt, K2CO3; (d) MeOH:H2O:THF (2:1:2), rt, LiOH; (e) DMF, rt, HOBT, DCC; (f) DMF, 0° C., NH2NH2•H2O; (g) EtOH, rt, aldehyde of interest, MgSO4; (h) MeOH, rt, NaBH3CN, conc. HCl As shown in Scheme 3, a cinnamamide derivative can be formed by refluxing 4-(aminomethyl)benzoic acid in acidified methanol (Scheme 3, reaction a). Cinnamoyl chloride can be formed using cinnamic acid and performing an acyl chlorination using oxalyl chloride in methylene chloride with catalytic amounts of dimethylformamide (Scheme 3, reaction b). The product of this reaction can be mixed with the benzoate from reaction a in a 1:1 (v/v) mixture of ethyl acetate and water with potassium carbonate to form the corresponding amide bond (Scheme 3, reaction c). This compound can be reacted with lithium hydroxide in a solution of methanol, water, and tetrahydrofuran (2:1:2 v/v) to generate the corresponding carboxylic acid (Scheme 3, reaction d). Reactions c and d can be combined using lithium hydroxide in place of potassium carbonate in reaction c to cleave the methyl ester while also simultaneously forming the amide bond. With the carboxylic acid generated, an amine coupling can be formed with HOBT and DCC in dimethylformamide (Scheme 3, reaction e). This intermediate can then be reacted with a hydrazine water salt at 0° C. Finally, the hydrazide can be reacted with the aldehyde of interest in ethanol with addition of magnesium sulfate and subsequently reduced using sodium cyanoborohydride in acidified methanol to yield compounds 3a-3e (Scheme 3, reactions f and g).

The invention will now be further described in the Examples below, which are intended as an illustration only and do not limit the scope of the invention.

EXAMPLES

All reagents and chemical solvents were used from the respective commercially available sources without further purification. 1H NMR and 13C NMR data were collected in deuterated solvent with a Bruker 400 MHz with Trimethylsilane as a standard reference. Chemical shifts are given in parts per million. NMR descriptions use the following abbreviations: s=singlet, d=doublet, t=triplet, q=quartet, m=multiplet, and br=broad peak. Coupling constants (J) reported in Hz. Mass spectra data were gathered using a Thermo LCQ Fleet mass spectrometer using electrospray ionization. Purification was performed using a Teledyne Isco Combiflash 200 on prepacked C18 columns. All target compounds were at least 95% pure confirmed via both UV detection of ESI-LCMS and 1H and 13C NMR. All assays were performed with <0.1% (v/v) DMSO.

The following abbreviations are used: AcOEt, Ethyl Acetate; DCC, N—N'-Dicyclochexylcarbodiimide; DMF, dimethylformamide; EtOH, Ethanol; HDAC, Histone Deacetylase; HH3, Histone H3; HH4, Histone H4; HOBT, Hydroxybenzotriazole; HLM, Human Liver Microsomes; LiOH, Lithium Hydroxide; $MgSO_4$, Magnesium Sulfate; MeOH, Methanol; $NaBH_3CN$, MM, Multiple Myeloma; Sodium Cyanoborohydride; PTM, Post-Translational Modification; and rt, Room Temperature.

Example 1

Synthesis of Butylhydrazide Derivatives (Compounds 1a-1l)

Series 1 General Procedure. As shown in Scheme 1, we began with either an aromatic carboxylic acid, acyl chloride, or ester. Using commercially available starting materials, we generated the corresponding hydrazide molecule through reactions a, b, and c, depending on the composition of the starting molecule. Target hydrazide compounds were reacted with butylaldehyde to generate the compound of interest. Carboxylic acids were reacted with oxalyl chloride in methylene chloride with catalytic amounts of dimethylformamide (Scheme 1, reaction a). The resulting acyl chloride, or commercially purchased acyl chlorides were stirred in methanol to give the corresponding methyl ester (Scheme 1, reaction b). The generated or commercially purchased methyl esters were refluxed in methanol with a hydrazine water salt to generate a hydrazide of interest (Scheme 1, reaction c). 1.1 equivalents of butaldehyde and 10 equivalents of magnesium sulfate were stirred in 10 mLs of ethanol with the hydrazide. The reaction was stirred at room temperature and monitored via TLC. After disappearance of starting material, the excess magnesium sulfate was removed via vacuum filtration, and the collected solution condensed under vacuum. The intermediate was resuspended in 4 mLs of methanol followed by addition of 1.2 equivalents of sodium cyanoborohydride and a pinch of methyl orange. Argon was bubbled through the resulting yellow solution for 5 minutes. At this time a solution of concentrated HCl in methanol (1:1 v/v) was added dropwise until the solution turned and stayed red. The mixture was allowed to stir overnight under argon. Volatiles were removed under vacuum and purified on silica gel eluted with acetonitrile and water to yield the desired product.

N'-butyl-4-methoxybenzohydrazide (1a)

498.54 mg (3 mmol) of 4-methoxybenzohydrazide was reacted as described in Series 1 General Procedure to yield 317.9 mg of dry product (48% yield). $^1$H NMR (400 MHz, DMSO): δ 9.89 (s, 1H), 7.82 (d, J=8.8 Hz, 2H), 6.99 (d, J=8.8 Hz, 2H), 4.99 (s, 1H), 3.81 (s, 3H), 2.79-2.76 (m, 2H), 1.48-1.40 (m, 2H), 1.38-1.32 (m, 2H), 0.89 (t, J=7.2 Hz, 3H). $^{13}$C NMR (100 MHz, DMSO): δ 165.4, 162.0, 129.3, 125.9, 114.0, 55.8, 51.5, 30.3, 20.3, 14.3. [(m+H$^+$)/z=223.25]. ($λ_{254}$) purity 95.4%, $t_R$ 9.28 mins.

N'-butylbenzofuran-2-carbohydrazide (1b)

324.0 mg (2 mmol) of benzofuran-2-carboxylic acid was suspended in 5 mLs of methylene chloride. The flask was flushed with argon for 10 minutes before injection of 0.4 mL (4 mmol) oxalyl chloride. Two drops of dimethylformamide were injected and furious bubbling began. The sealed vessel was continuously flushed with argon and vented for 2 hours at room temperature. 10 mLs of sieve dried ethanol was slowly injected and allowed to stir for an additional hour. Volatiles were removed under vacuum and the crude intermediate was resuspended in 5 mLs ethanol. To this solution was added 250 mg (5 mmol) of hydrazine water salt. The reaction was refluxed for 3 hours to give the corresponding hydrazide. Volatiles were removed under vacuum and the product suspended in 10 mLs of ethanol. From here the reaction proceeded as described in Series 1 General Procedure to yield 369.1 mg of dry product (72% yield). $^1$H NMR (400 MHz, DMSO): δ 10.26 (d, J=6.0 Hz, 1H), 7.78 (d, J=8.0 Hz, 1H), 7.66 (d, J=8.4 Hz, 1H), 7.54 (s, 1H), 7.49-7.45 (m, 1H), 7.36-7.32 (m, 1H), 5.16-5.13 (m, 1H), 2.84-2.79 (m, 2H), 1.48-1.41 (m, 2H), 1.39-1.33 (m, 2H), 0.90 (t, J=7.2 Hz, 3H); $^{13}$C NMR (100 MHz, DMSO): δ 157.7, 154.7, 148.7, 127.5, 127.2, 124.2, 123.1, 112.2, 109.6, 51.2, 30.2, 20.3, 14.4. [(m+H$^+$)/z=233.25]. ($λ_{254}$) purity 98.8%, $t_R$ 11.53 mins.

N'-butyl-4-phenoxybenzohydrazide (1c)

685 mg (3 mmol) of 4-phenoxybenzohydrazide was suspended in 10 mLs of ethanol From here the reaction proceeded as described in Series 1 General Procedure to yield 596.7 mg of dry product (70% yield). $^1$H NMR (400 MHz, DMSO): δ 9.99 (s, 1H), 7.88 (d, J=8.8 Hz, 2H), 7.46-7.42 (m, 2H), 7.23-7.20 (m, 1H), 7.09 (d, J=8.0 Hz, 2H), 7.03 (d, J=8.8 Hz, 2H), 5.07 (s, 1H), 2.81-2.77 (m, 2H), 1.47-1.41 (m, 2H), 1.38-1.32 (m, 2H), 0.89 (t, J=7.2 Hz, 3H); $^{13}$C NMR (100 MHz, DMSO): δ 165.1, 159.9, 156.1, 130.7, 129.7, 128.4, 124.7, 119.9, 117.9, 51.4, 30.3, 20.3, 14.4. [(m+H$^+$)/z=285.25]. ($\lambda_{254}$) purity 98.2%, $t_R$ 12.60 mins.

N'-butylnicotinohydrazide (1d)

1068 mg (6 mmol) of nicotinoyl chloride was suspended in 20 mLs of methanol. To this solution was added 1.7 mL (12 mmol) of triethylamine. The reaction was stirred at room temperature for 1 hour. 750 mg (15 mmol) hydrazine water salt was added and the solution was refluxed for 3 hours yielding the corresponding hydrazide. Volatiles were removed under vacuum and the intermediate was resuspended in 30 mLs of methanol. From here the reaction proceeded as described in Series 1 General Procedure to yield 721.7 mg of dry product (62% yield). $^1$H NMR (400 MHz, DMSO): δ 10.21 (s, 1H), 8.99 (s, 1H), 8.72-8.70 (m, 1H), 8.19-8.10 (m, 1H), 7.52-7.49 (m, 1H), 5.15 (s, 1H), 2.83-2.79 (m, 2H), 1.48-1.42 (m, 2H), 1.38-1.32 (m, 2H), 0.89 (t, J=7.2 Hz, 3H); $^{13}$C NMR (100 MHz, DMSO): δ 164.2, 152.3, 148.6, 135.2, 129.3, 124.0, 51.3, 30.2, 20.3, 14.4. [(m+H$^+$)/z=194.25]. ($\lambda_{254}$) purity 95.6%, $t_R$ 6.17 mins.

N'-butyl-[1,1'-biphenyl]-4-carbohydrazide (1e)

890 mg (3.8 mmol) of methyl [1,1']-biphenyl-4-carboxylate was suspended in 20 mLs of methanol. To this solution, 945 mg (18.9 mmol) of hydrazine water salt was added. The solution was brought to reflux and reacted for 3 hours. The solution was cooled and volatiles evaporated under vacuum. From here the reaction proceeded as described in Series 1 General Procedure to yield 555.1 mg of dry product (54% yield). $^1$H NMR (400 MHz, DMSO): δ 10.08 (d, J=6 Hz, 1H), 7.94-7.92 (m, 2H), 7.78-7.73 (m, 4H), 7.52-7.48 (m, 2H), 7.44-7.40 (m, 1H), 5.13-5.09 (m, 1H), 2.84-2.79 (m, 2H), 1.49-1.42 (m, 2H), 1.40-1.35 (m, 2H), 0.91 (t, J=7.2 Hz, 3H); $^{13}$C NMR (100 MHz, DMSO): δ 165.4, 143.2, 139.6, 132.5, 129.5, 128.5, 128.2, 127.3, 127.0, 51.4, 30.3, 20.3, 14.4. [(m+H$^+$)/z=269.25]. ($\lambda_{254}$) purity 96.7%, $t_R$ 12.82 mins.

N'-butylthiophene-2-carbohydrazide (1f)

1500 mg (10 mmol) of thiophene-2-carbonyl chloride was injected into 10 mLs of sieve dried methanol and bubbled with argon for 10 minutes. To this mixture was injected two drops of dimethylformamide. The reaction proceeded at room temperature for 1 hour before addition of 600 mg (12 mmol) hydrazine water salt. The solution was refluxed for 3 hours before being cooled and condensed in vacuo. The reaction then proceeded as described in Series 1 General Procedure to yield 1235 mg of dry product (62% yield). $^1$H NMR (400 MHz, DMSO): δ 10.02 (s, 1H), 7.76-7.74 (m, 2H), 7.15-7.13 (m, 1H), 5.03 (s, 1H), 2.80-2.77 (m, 2H), 1.45-1.40 (m, 2H), 1.37-1.32 (m, 2H), 0.89 (m, J=7.2 Hz, 3H); $^{13}$C NMR (100 MHz, DMSO): δ 161.0, 138.8, 131.0, 128.4, 128.2, 51.3, 30.3, 20.3, 14.4. [(m+H$^+$)/z=199.17]. ($\lambda_{254}$) purity 97.5%, $t_R$ 8.47 mins.

N'-butylfuran-2-carbohydrazide (1g)

1100 mg (8.4 mmol) of furan-2-carbonyl chloride was injected into 10 mL of sieve dried methanol that was bubbled with argon for 10 minutes prior to addition. To this mixture was injected 1780 mg (17.6 mmol) of triethylamine. After 60 minutes, 1000 mg (20 mmol) of hydrazine water salt was added, and heated to reflux for 3 hours. The reaction was cooled and condensed under vacuum. From here the reaction proceeded as described in Series 1 General Procedure to yield 861 mg of dry product (56% yield). $^1$H NMR (400 MHz, DMSO): δ 9.90 (s, 1H), 7.83-7.82 (m, 1), 7.11-7.10 (m, 1H), 6.62-6.60 (m, 1H), 5.00 (s, 1H), 2.79-2.74 (m, 2H), 1.44-1.40 (m, 2H), 1.38-1.30 (m, 2H), 0.88 (t, J=7.2 Hz, 3H); $^{13}$C NMR (100 MHz, DMSO): δ 157.6, 147.3, 145.4, 113.6, 112.1, 51.3, 30.2, 20.3, 14.4. [(m+H$^+$)/z=183.17]. ($\lambda_{254}$) purity 98.4%, $t_R$ 7.43 mins.

N'-butyl-3-phenylpropanehydrazide (1h)

1012 mg (6 mmol) of 3-phenylpropanoyl chloride was injected into 10 mLs of argon bubbled, sieve dried methanol. The reaction was allowed to stir for 1 hour before addition of 900 mg (18 mmol) hydrazine water salt. The mixture was brought to reflux for 3 hours before being cooled to room temperature and condensed under vacuum. From here the reaction proceeded as described in Series 1 General Procedure to yield 911 mg of dry product (68% yield). $^1$H NMR (400 MHz, DMSO): δ 9.25 (s, 1H), 7.29-7.25 (m, 2H), 7.21-7.26 (m, 3H), 4.77 (s, 1H), 2.82 (t, J=7.6 Hz, 2H), 2.63-2.59 (m, 2H), 2.33 (t, J=7.6 Hz, 2H), 1.31-1.25 (m, 4H), 0.85 (t, J=7.2 Hz, 3H); $^{13}$C NMR (100 MHz, DMSO): δ 170.5, 141.5, 128.7 (d), 126.3, 51.2, 35.6, 31.5, 30.1, 20.2, 14.4. [(m+H$^+$)/z=221.25]. ($\lambda_{254}$) purity 98.9%, $t_R$ 8.56 mins.

N'-butylcinnamohydrazide (1i)

1480 mg (10 mmol) of trans-cinnamic acid was suspended in 50 mLs of acetonitrile. To this solution was added 1620 mg (12 mmol) of 1-hydroxybenzotriazole and 2478 mg (12 mmol) N, N'-dicyclohexylcarbodiimide. The solution stirred overnight at room temperature before addition of 600 mg (12 mmol) hydrazine water salt, which was refluxed for 3 hours. The solution was brought to room temperature and condensed under vacuum. From here the reaction proceeded as described in Series 1 General Procedure to yield 885 mg of dry product (40% yield). $^1$H NMR (400 MHz, DMSO): δ 9.62 (s, 1H), 7.58-7.56 (m, 2H), 7.45-7.38 (m, 4H), 6.57 (d, J=16.0 Hz, 1H), 5.05 (s, 1H), 2.76-2.72 (m, 2H), 1.44-1.28 (m, 4H), 0.89 (t, J=7.2 Hz, 3H); $^{13}$C NMR (100 MHz, DMSO): δ 164.3, 139.0, 135.4, 129.9, 129.4, 127.9, 120.8, 51.4, 30.2, 20.2, 14.4. [(m+H$^+$)/z=219.25]. ($\lambda_{254}$) purity 97.5%, $t_R$ 10.95 mins.

N'-butyl-1-napthohydrazide (1j)

1033 mg (6 mmol) of 1-napthoic acid was suspended in 20 mLs of argon flushed methylene chloride. To this solution was injected 1143 mg (9 mmol) of oxalyl chloride followed by injection of 2 drops of dimethylformamide. Furious bubbling was seen, with gas being exhausted and argon flushing continually through the room temperature reaction. After one hour, 20 mLs of sieve dried methanol was injected slowly. After reacting for an additional hour at room temperature, the solution was condensed under vacuum and resuspended in 30 mLs of methanol. To this was added 1500 mg (30 mmol) of hydrazine water salt. The reaction was brought to reflux for 3 hours before being cooled and condensed under vacuum. From here the reaction proceeded as described in Series 1 General Procedure to yield 1050 mg of dry product (72% yield). $^1$H NMR (400 MHz, DMSO): δ

9.97 (s, 1H), 8.22-8.19 (m, 1H), 8.04-7.98 (m, 2H), 7.61-7.53 (m, 4H), 5.23 (s, 1H), 2.92-2.87 (m, 2H), 1.53-1.42 (m, 2H), 1.40-1.38 (m, 2H), 0.93 (t, J=7.2 Hz, 3H); $^{13}$C NMR (100 MHz, DMSO): δ 167.8, 133.7, 133.6, 130.4, 130.4, 128.7, 127.2, 126.7, 125.8, 125.7, 125.5, 51.3, 30.3, 20.3, 14.4. [(m+H$^+$)/z=243.25]. ($\lambda_{254}$) purity >99%, $t_R$ 11.00 mins.

N'-butyl-2-napthohydrazide (1k)

1120 mg (6 mmol) of 2-napthohydrazide was reacted as described in Series 1 General Procedure to yield 1016 mg of dry product (70% yield). $^1$H NMR (400 MHz, DMSO): δ 10.2 (s, 1H), 8.46 (s, 1H), 8.04-7.93 (m, 4H), 7.64-7.58 (m, 2H), 5.17 (s, 1H), 2.87-2.83 (m, 2H), 1.51-1.46 (m, 2H), 1.41-1.35 (m, 2H), 0.91 (t, J=7.2 Hz, 3H); $^{13}$C NMR (100 MHz, DMSO): δ 165.8, 134.6, 132.6, 131.1, 129.3, 128.4, 128.1, 128.0, 127.8, 127.2, 124.4, 51.4, 30.3, 20.3, 14.4. [(m+H$^+$)/z=243.25]. ($\lambda_{254}$) purity >99%, $t_R$ 11.42 mins.

N-(4-(2-butylhydrazine-1-carbonyl)benzyl)benzamide (1l)

To a mixture of sieve dried methylene chloride, was added 711 mg (4 mmol) of methyl 4-(aminoethyl)benzoate. This vessel was flushed with argon for 30 minutes before injection of 560 mg (4 mmol) of benzoyl chloride and 607 mg (6 mmol) of trimethylamine. The reaction was stirred at room temperature for 2 hours before being condensed under vacuum. The crude intermediate was resuspended in 30 mLs of methanol and 1000 mg (20 mmol) of hydrazine water salt was added as one portion. The solution was refluxed for 3 hours before being cooled and condensed under vacuum. From here the reaction proceeded as described in Series 1 General Procedure to yield 601 mg of dry product (46% yield). $^1$H NMR (400 MHz, DMSO): δ 9.99 (s, 1H), 9.13-9.10 (t, J=6.0 Hz, 1H), 7.93-7.91 (m, 2H), 7.81-7.79 (m, 2H), 7.57-7.47 (m, 3H), 7.41-7.39 (m, 2H), 5.07 (s, 1H), 4.54 (d, J=6.0 Hz, 2H); $^{13}$C NMR (100 MHz, DMSO): δ 166.7, 165.6, 143.5, 134.7, 132.2, 131.8, 128.8, 12.7, 127.6, 127.5, 51.4, 42.9, 30.3, 20.3, 14.4. HRMS-ESI [(m+H$^+$)/z] calculated for C$_{19}$H$_{23}$N$_3$O$_2$: 326.18697; found, 326.18622. ($\lambda_{254}$) purity 96.3%, $t_R$ 11.92 mins.

Example 2

Synthesis of N-(4-(hydrazide)benzyl)benzamide derivatives (Compounds 2a-2m)

Intermediate Formation.

6050 mg (40 mmol) of 4-(aminomethyl)benzoic acid was dissolved in 200 mL of methanol, to which was added 6 mLs of concentrated HCl in one portion. The mixture was refluxed overnight and the volatiles condensed under vacuum. The resulting white solid was suspended in ethyl ether and separated via vacuum filtration to yield the benzoate HCl salt. This compound was dissolved in a 1:2 mixture of ethyl acetate and water and chilled to 0° C. to which 11040 mg (80 mmol) was added followed by addition of 5623 mg benzoyl chloride (40 mmol). The vessel was warmed to room temperature and stirred for 2 additional hours. The mixture was separated via acid/base extraction, washing the water phase twice with ethyl acetate. All organic phases were combined and condensed under vacuum to yield a white solid. This was suspended in 200 mL of methanol and 10000 mg (200 mmol) of hydrazine water salt was added. The solution was refluxed for 48 hours, cooled to room temperature, and volatiles were removed under vacuum. This intermediate N-(4-(hydrazinecarbonyl)benzyl)benzamide (2sm) was used as the starting material for all further reactions for this family.

Series 2 General Procedure.

The mixture of 2sm and aldehyde of interest were stirred at room temperature overnight; vacuum filtration afforded the desired intermediate, which was dissolved in 30 mL of methanol. To this solution was added a pinch of Methyl Orange, and the solution's color turned yellow. The solution was bubbled under argon for 5 minutes, and 2.2 mmol of sodium cyanoborohydride was then added to it. A 1:1 mixture of methanol and concentrated HCl was added dropwise until the solution turned red. After addition, the mixture was stirred at room temperature for 6 hours. The reaction was quenched with sodium hydroxide, and organic solvents were removed under vacuum. The residues were extracted twice with ethyl acetate, and organic phases were combined and dried over magnesium sulfate. After filtration, organic solvents were removed and the residues were purified by flash chromatography.

(E)-N-(4-(2-(but-2-en-1-yl)hydrazine-1-carbonyl)benzyl)benzamide (2a)

2 mmol of 2sm was dissolved in 100 mL ethanol with ultra-sonication aid. To this solution was added 40 mmol of magnesium sulfate and 2 mmol of (E)-but-2-enal. From here the reaction proceeded as described in Series 2 General Procedure to yield 208 mg (32% yield). $^1$H NMR (400 MHz, DMSO): δ 9.97 (d, J=5.6 Hz, 1H), 9.12 (t, J=6.0 Hz, 1H), 7.93-7.91 (m, 2H), 7.81-7.78 (m, 2H), 7.58-7.48 (m, 3H), 7.41-7.39 (m, 2H), 5.63-5.50 (m, 2H), 5.11-5.07 (m, 1H), 4.54 (d, J=6.0 Hz, 2H), 3.37-3.35 (m, 2H), 1.65 (d, J=5.6 Hz, 3H); $^{13}$C NMR (100 MHz, DMSO): δ 166.8, 165.7, 143.5, 134.7, 132.2, 131.8, 128.8, 128.4, 128.2, 127.7, 127.6, 127.5, 53.6, 42.9, 18.2. [(m+H$^+$)/z=324.17]. ($\lambda_{254}$) purity >99%, $t_R$ 10.00 mins.

N-(4-(2-isopropylhydrazine-1-carbonyl)benzyl)benzamide (2b)

2 mmol of 2sm was dissolved in 100 mL ethanol with ultra-sonication aid. To this solution was added 40 mmol of magnesium sulfate and 2 mmol of isopropanal. From here the reaction proceeded as described in Series 2 General Procedure to yield yielded 324 mg (52% yield). $^1$H NMR (400 MHz, DMSO): δ 9.95 (d, J=6.8 Hz, 1H), 9.11 (t, J=6.0 Hz, 1H), 7.92-7.90 (m, 2H), 7.82-7.80 (m, 2H), 7.58-7.48 (m, 3H), 7.41-7.39 (m, 2H), 4.95-4.92 (m, 1H), 4.53 (d, J=6.0 Hz, 2H), 3.11-3.03 (m, 1H), 1.02 (d, J=10.4 Hz, 6H); $^{13}$C NMR (100 MHz, DMSO): δ 166.8, 166.0, 143.5, 134.7, 132.2, 131.8, 128.8, 127.7, 127.6, 127.4, 50.8, 42.9, 21.4. [(m+H$^+$)/z=312.25]. ($\lambda_{254}$) purity 98.8%, $t_R$ 8.68 mins.

(E)-N-(4-(2-propylidenehydrazine-1-carbonyl)benzyl)benzamide (2c)

2 mmol of 2sm was dissolved in 100 mL ethanol with ultra-sonication aid. To this solution was added 40 mmol of magnesium sulfate and 2 mmol of propanal. From here the reaction proceeded as described in Series 2 General Procedure to yield 347 mg (56% yield). $^1$H NMR (400 MHz, DMSO): δ 11.39 (s, 1H), 9.13 (t, J=6.0 Hz, 1H), 7.93-7.90 (m, 2H), 7.84-7.75 (m, 3H), 7.58-7.38 (m, 5H), 4.56-4.53 (m, 2H), 2.30-2.25 (m, 2H), 1.06 (t, J=7.2 Hz, 3H); $^{13}$C NMR (100 MHz, DMSO): δ 166.8, 163.1, 153.5, 143.9, 134.7, 131.8, 128.8, 128.1, 127.7, 127.5 (d), 42.9, 25.9, 11.1. HRMS-ESI [(m+H$^+$)/z] calculated for $C_{18}H_{19}N_3O_2$: 310.15567; found, 310.15529. ($\lambda_{254}$) purity 97.5%, $t_R$ 11.60 mins.

N-(4-(2-propylhydrazine-1-carbonyl)benzyl)benzamide (2d)

2 mmol of 2sm was dissolved in 100 mL ethanol with ultra-sonication aid. To this solution was added 40 mmol of magnesium sulfate and 2 mmol of propanal. From here the reaction proceeded as described in Series 2 General Procedure to yield 318 mg (51% yield). $^1$H NMR (400 MHz, DMSO): δ 9.98 (d, J=6.0 Hz, 1H), 9.11 (t, J=6.0 Hz, 1H), 7.92-7.91 (m, 2H), 7.81-7.79 (m, 2H), 7.56-7.48 (m, 3H), 7.41-7.39 (m, 2H), 5.11-5.07 (m, 1H), 4.53 (d, J=6.0 Hz, 2H), 2.78-2.73 (m, 2H), 1.49-1.44 (m, 2H), 0.92 (t, J=7.6 Hz, 3H); $^{13}$C NMR (100 MHz, DMSO): δ 166.7, 165.6, 143.5, 134.7, 132.2, 131.8, 128.8, 127.7, 127.6, 127.4, 53.6, 42.9, 21.3, 12.1. HRMS-ESI [(m+H$^+$)/z] calculated for $C_{18}H_{21}N_3O_2$: 312.17132; found, 312.17127. ($\lambda_{254}$) purity >99%, $t_R$ 12.28 mins.

N-(4-(2-pentylhydrazine-1-carbonyl)benzyl)benzamide (2e)

2 mmol of 2sm was dissolved in 100 mL ethanol with ultra-sonication aid. To this solution was added 40 mmol of magnesium sulfate and 2 mmol of pentanal. From here the reaction proceeded as described in Series 2 General Procedure to yield 312 mg (46% yield). $^1$H NMR (400 MHz, DMSO): δ 9.99 (s, 1H), 9.11 (t, J=6.0 Hz, 1H), 7.93-7.91 (m, 2H), 7.81-7.79 (m, 2H), 7.57-7.47 (m, 3H), 7.41-7.39 (m, 2H), 5.07 (s, 1H), 4.53 (d, J=6.0 Hz, 2H), 2.78 (s, 2H), 1.48-1.44 (m, 2H), 1.33-1.29 (m, 4H), 0.88 (t, J=6.8 Hz, 3H); $^{13}$C NMR (100 MHz, DMSO): δ 166.8, 165.6, 143.5, 134.7, 132.2, 131.8, 128.8, 127.7, 127.6, 127.5, 51.7, 42.9, 29.4, 27.8, 22.5, 14.4. [(m+H$^+$)/z=340.25]. ($\lambda_{254}$) purity >99%, $t_R$ 11.30 mins.

N-(4-(2-(3,3,3-trifluoropropyl)hydrazine-1-carbonyl)benzyl)benzamide (2f)

2 mmol of 2sm was dissolved in 100 mL ethanol with ultra-sonication aid. To this solution was added 40 mmol of magnesium sulfate and 2 mmol of 3,3,3-trifluoropropanal. From here the reaction proceeded as described in Series 2 General Procedure to yield 445 mg (61% yield). $^1$H NMR (400 MHz, DMSO): δ 10.03 (d, J=6.0 Hz, 1H), 9.11 (t, J=6.0 Hz, 1H), 7.92-7.90 (m, 2H), 7.82-7.80 (m, 2H), 7.58-7.48 (m, 3H), 7.42-7.40 (m, 2H), 5.43-5.39 (m, 1H), 4.54 (d, J=6.0 Hz, 2H), 3.05-3.00 (m, 2H), 2.54-2.44 (m, 2H); $^{13}$C-HSQC (100 MHz, 400 MHz, DMSO) δ 131.8, 128.8, 127.7, 127.6, 127.5, 44.55, 42.8, 32.1. [(m+H$^+$)/z=366.25]. ($\lambda_{254}$) purity 97.7%, $t_R$ 10.85 mins.

N-(4-(2-(cyclopropylmethyl)hydrazine-1-carbonyl)benzyl)benzamide (2g)

2 mmol of 2sm was dissolved in 100 mL ethanol with ultra-sonication aid. To this solution was added 40 mmol of magnesium sulfate and 2 mmol of cyclopropanecarbaldehyde. From here the reaction proceeded as described in Series 2 General Procedure to yield 415 mg (64% yield). $^1$H NMR (400 MHz, DMSO): δ 10.06 (s, 1H), 9.13 (s, 1H), 7.93-7.92 (m, 2H), 7.85-7.80 (m, 2H), 7.57-7.47 (m, 3H), 7.41-7.39 (m, 2H), 5.12 (s, 1H), 4.55 (s, 2H), 2.66 (s, 2H), 0.93-0.91 (m, 1H), 0.46-0.44 (m, 2H), 0.16-0.15 (m, 2H); $^{13}$C NMR (100 MHz, DMSO): δ 166.8, 165.5, 143.5, 134.7, 132.2, 131.8, 128.8, 127.7, 127.6, 127.5, 56.6, 42.9, 9.95, 3.61. [(m+H$^+$)/z=324.17]. ($\lambda_{254}$) purity 97.4%, $t_R$ 9.27 mins.

N-(4-(2-heptylhydrazine-1-carbonyl)benzyl)benzamide (2h)

2 mmol of 2sm was dissolved in 100 mL ethanol with ultra-sonication aid. To this solution was added 40 mmol of magnesium sulfate and 2 mmol of heptanal. From here the reaction proceeded as described in Series 2 General Procedure to yield 345 mg (47% yield). $^1$H NMR (400 MHz, DMSO): δ 10.00 (s, 1H), 9.12 (t, J=6.0 Hz, 1H), 7.93-7.91 (m, 2H), 7.82-7.80 (m, 2H), 7.57-7.47 (m, 3H), 7.41-7.39 (m, 2H), 5.08-5.05 (m, 1H), 4.54 (d, J=6.0 Hz, 2H), 2.81-2.76 (m, 2H), 1.48-1.44 (m, 2H), 1.34-1.26 (m, 8H), 0.86 (t, J=6.4 Hz, 3H); $^{13}$C NMR (100 MHz, DMSO): δ 166.7, 165.6, 143.5, 134.7, 132.2, 131.8, 128.8, 127.7, 127.6, 127.4, 51.7, 42.9, 31.8, 29.1, 28.1, 27.1, 22.6, 14.4. [(m+H$^+$)/z=368.33]. ($\lambda_{254}$) purity >99%, $t_R$ 13.25 mins.

N-(4-(2-octylhydrazine-1-carbonyl)benzyl)benzamide (2i)

2 mmol of 2sm was dissolved in 100 mL ethanol with ultra-sonication aid. To this solution was added 40 mmol of magnesium sulfate and 2 mmol of octanal. From here the reaction proceeded as described in Series 2 General Procedure to yield 305 mg (40% yield). $^1$H NMR (400 MHz, DMSO): δ 10.00 (s, 1H), 9.12 (t, J=6.0 Hz, 1H), 7.93-7.91 (m, 2H), 7.82-7.80 (m, 2H), 7.55-7.46 (m, 3H), 7.41-7.39 (m, 2H), 5.07-5.06 (m, 1H), 4.54 (d, J=5.6 Hz, 2H), 2.80-2.76 (m, 2H), 1.47-1.42 (m, 2H), 1.34-1.25 (m, 10H), 0.86 (t, J=6.4 Hz, 3H); $^{13}$C NMR (100 MHz, DMSO): δ 166.7, 165.6, 143.5, 134.7, 132.2, 131.8, 128.8, 127.7, 127.6, 127.4, 51.7, 42.9, 31.7, 29.4, 29.2, 28.1, 27.2, 22.6, 14.4. [(m+H$^+$)/z=382.33]. ($\lambda_{254}$) purity 95.8%, $t_R$ 13.97 mins.

N-(4-(2-hexylhydrazine-1-carbonyl)benzyl)benzamide (2j)

2 mmol of 2sm was dissolved in 100 mL ethanol with ultra-sonication aid. To this solution was added 40 mmol of magnesium sulfate and 2 mmol of hexanal. From here the reaction proceeded as described in Series 2 General Procedure to yield 367 mg (52% yield). $^1$H NMR (400 MHz, DMSO): δ 9.99 (s, 1H), 9.12 (t, J=6.0 Hz, 1H), 7.93-7.91 (m, 2H), 7.81-7.79 (m, 2H), 7.58-7.47 (m, 3H), 7.41-7.39 (m, 2H), 5.08-5.05 (m, 1H), 4.54 (d, J=6.0 Hz, 2H), 2.81-2.76 (m, 2H), 1.49-1.42 (m, 2H), 1.37-1.26 (m, 6H), 0.87 (t, J=6.4 Hz, 3H); $^{13}$C NMR (100 MHz, DMSO): δ 166.7, 165.6, 143.5, 134.7, 132.2, 131.8, 128.8, 127.7, 127.6, 127.4, 51.7, 42.9, 31.7, 28.1, 26.8, 22.6, 14.4. [(m+H$^+$)/z=354.33]. ($\lambda_{254}$) purity 98.8%, $t_R$ 12.45 mins.

N-(4-(2-decylhydrazine-1-carbonyl)benzyl)benzamide (2k)

2 mmol of 2sm was dissolved in 100 mL ethanol with ultra-sonication aid. To this solution was added 40 mmol of magnesium sulfate and 2 mmol of decanal. From here the reaction proceeded as described in Series 2 General Procedure to yield 295 mg (36% yield). $^1$H NMR (400 MHz, DMSO): δ 9.99 (s, 1H), 9.12 (t, J=6.0 Hz, 1H), 7.93-7.91 (m, 2H), 7.81-7.79 (m, 2H), 7.57-7.54 (m, 3H), 7.41-7.39 (m, 2H), 5.07-5.05 (m, 1H), 4.54 (d, J=6.0 Hz, 2H), 2.80-2.75

(m, 2H), 1.48-1.42 (m, 2H), 1.33-1.25 (m, 14H), 0.86 (t, J=6.8 Hz, 3H); $^{13}$C NMR (100 MHz, DMSO): δ 166.7, 165.6, 143.5, 134.7, 132.2, 131.8, 128.8, 127.7, 127.5, 127.4, 51.7, 42.9, 31.8, 29.5 (d), 29.2, 28.1, 27.2, 22.6, 14.4. [(m+H$^+$)/z=410.33]. ($\lambda_{254}$) purity 98.2%, $t_R$ 15.01 mins.

N-(4-(2-ethylhydrazine-1-carbonyl)benzyl)benzamide (2l)

2 mmol of 2sm was dissolved in 100 mL ethanol with ultra-sonication aid. To this solution was added 40 mmol of magnesium sulfate and 2 mmol of acetaldehyde. From here the reaction proceeded as described in Series 2 General Procedure to yield 404 mg (68% yield). $^1$H NMR (400 MHz, DMSO): δ 10.00 (s, 1H), 9.13-9.11 (m, 1H), 7.93-7.90 (m, 2H), 7.81-7.89 (m, 2H), 7.56-7.47 (m, 3H), 7.42-7.39 (m, 2H), 5.07 (s, 1H), 4.54 (s, 2H), 2.83-2.80 (m, 2H), 1.06-1.02 (m, 3H); $^{13}$C NMR (100 MHz, DMSO): δ 166.8, 165.7, 143.5, 134.7, 132.2, 131.8, 128.8, 127.7, 127.6, 127.5, 46.0, 42.9, 13.6. [(m+H$^+$)/z=298.25]. ($\lambda_{254}$) purity 95.6%, $t_R$ 7.71 mins.

N-(4-(2-(cyclobutylmethyl)hydrazine-1-carbonyl)benzyl)benzamide (2m)

2 mmol of 2sm was dissolved in 100 mL ethanol with ultra-sonication aid. To this solution was added 40 mmol of magnesium sulfate and 2 mmol of cyclobutanecarbaldehyde. From here the reaction proceeded as described in Series 2 General Procedure to yield 438 mg (65% yield). $^1$H NMR (400 MHz, DMSO): δ 9.97 (s, 1H), 9.14-9.10 (m, 1H), 7.93-7.91 (m, 2H), 7.80-7.78 (m, 2H), 7.58-7.48 (m, 3H), 7.40-7.38 (m, 2H), 5.06 (s, 1H), 4.53 (d, J=6.0 Hz, 2H), 2.83 (d, J=7.2 Hz, 2H), 2.49-2.43 (m, 1H), 2.05-2.03 (m, 2H), 1.89-1.78 (m, 2H), 1.74-1.65 (m, 2H); $^{13}$C NMR (100 MHz, DMSO): δ 166.7, 165.6, 143.5, 134.7, 132.2, 131.8, 128.8, 127.7, 127.5, 127.4, 57.5, 42.9, 34.2, 26.5, 18.8. [(m+H$^+$)/z=338.17]. ($\lambda_{254}$) purity 96.7%, $t_R$ 10.55 mins.

Example 3

Synthesis of N-(4-(hydrazide)benzyl)cinnamamide Derivatives (Compounds 3a-3e)

Intermediate Formation.

Transcinnamic acid (40 mmol) was dissolved in 500 mLs of methylene chloride. The apparatus was purged with argon and bubbled through the solution. To this solution was injected 60 mmol of oxalyl chloride and 10 drops of dimethylformamide. The mixture was stirred at room temperature for 3 hours under constant argon flush. The solution was condensed under vacuum and brought to 0° C. A pre-chilled 1:2 mixture of ethyl acetate and water was slowly added followed by addition of potassium carbonate (80 mmol) and methyl 4-(aminomethyl)benzoate HCl (40 mmol). The reaction was brought to room temperature slowly and allowed to stir for 2 additional hours. The water and organic phases were separated, and the water phase washed twice with ethyl acetate. The organic phases were combined and dried under vacuum. A white solid was obtained and used in the next step without further purification. The product was resuspended in a 2:2:1 solution of methanol, tetrahydrofuran, and water at 0° C. To this solution was cautiously added 48 lithium hydroxide (48 mmol). The solution was allowed to warm to room temperature and stir overnight. Volatiles were removed under vacuum and the residue was acidified with 1 M HCl before extraction with ethyl acetate; volatiles were once again removed under vacuum and lyophilized. The resulting white crystalline powder was used in the next step without further purification. The 4-(cinnamamidomethyl)benzoic acid generated in the above steps was suspended in 400 mLs of dimethylformamide, to which was added Hydroxybenzotriazole (80 mmol) and N—N'-Dicyclochexylcarbodiimide (80 mmol). This solution was stirred for 6 hours at RT before addition of hydrazine water salt (48 mmol) at 0° C. in one portion. The mixture was allowed to warm to room temperature and stir overnight before being extracted with 1200 mLs of water. The water phase was extracted with ethyl acetate twice, and the organic layers were combined and condensed under vacuum. The product N-(4-(hydrazinecarbonyl)benzyl)cinnamamide (3sm) was purified via flash chromatography to yield the corresponding hydrazide that will be used as a starting material for all further reactions for this family (3a-3e).

N-(4-(2-ethylhydrazine-1-carbonyl)benzyl)cinnamide (3a)

2 mmol of 3sm was dissolved in 100 mL ethanol with ultra-sonication aid. To this solution was added 40 mmol of magnesium sulfate and 2 mmol of ethanal. From here the reaction proceeded as described in Series 2 General Procedure to yield 454 mg (70% yield). $^1$H NMR (400 MHz, DMSO): δ 10.0 (s, 1H), 8.70 (t, J=5.9 Hz, 1H), 7.80 (d, J=8.2 Hz, 2H), 7.58 (d, J=6.8 Hz, 2H), 7.49 (d, J=15.8 Hz, 1H), 7.43-7.36 (m, 5H), 6.72 (d, J=15.8 Hz, 1H), 5.06 (s, 1H), 4.46 (d, J=6.0 Hz, 2H), 2.85-2.79 (m, 2H), 2.51 (t, J=1.7 Hz, 2H), 1.04 (t, J=7.2 Hz, 3H); $^{13}$C NMR (100 MHz, DMSO): δ 165.6, 165.5, 143.2, 139.6, 135.3, 132.3, 130.0, 129.4, 128.0, 127.6, 122.4, 46.0, 42.5, 13.6. [(m+H$^+$)/z=324.25]. ($\lambda_{254}$) purity 97.5%, $t_R$ 10.38 mins.

N-(4-(2-propylhydrazine-1-carbonyl)benzyl)cinnamamide (3b)

2 mmol of 3sm was dissolved in 100 mL ethanol with ultra-sonication aid. To this solution was added 40 mmol of magnesium sulfate and 2 mmol of propanal. From here the reaction proceeded as described in Series 2 General Procedure to yield 546 mg (81% yield). $^1$H NMR (400 MHz, DMSO): δ 10.00 (s, 1H), 8.70 (t, J=6.0 Hz, 1H), 7.82-7.80 (m, 2H), 7.60-7.58 (m, 2H), 7.50 (d, J=16 Hz, 1H), 7.45-7.37 (m, 5H), 6.72 (d, J=15.6, 1H), 5.11-5.08 (m, 1H), 4.47 (d, J=5.6 Hz, 2H), 2.78-2.74 (m, 2H), 1.51-1.45 (m, 2H), 0.92 (t, J=7.2 Hz, 3H); $^{13}$C NMR (100 MHz, DMSO): δ 165.6, 165.5, 143.2, 139.6, 135.3, 132.3, 130.0, 129.4, 128.0, 127.6 (d), 122.4, 53.6, 42.5, 21.3, 12.1. HRMS-ESI [(m+H$^+$)/z] calculated for $C_{20}H_{23}N_3O_2$: 338.18697; found, 338.18726. ($\lambda_{254}$) purity 98.4%, $t_R$ 12.42 mins.

N-(4-(2-butylhydrazine-1-carbonyl)benzyl)cinnamamide (3c)

2 mmol of 3sm was dissolved in 100 mL ethanol with ultra-sonication aid. To this solution was added 40 mmol of magnesium sulfate and 2 mmol of butanal. From here the reaction proceeded as described in Series 2 General Procedure to yield 576 mg (82% yield). $^1$H NMR (400 MHz, DMSO): δ 10.0 (s, 1H), 8.7 (t, J=6.0 Hz, 1H), 7.8 (d, J=8.3 Hz, 2H), 7.58 (d, J=6.8 Hz, 2H), 7.49 (d, J=15.8 Hz, 1H), 7.43-7.36 (m, 5H), 6.71 (d, J=15.8 Hz, 1H), 5.06 (s, 1H), 4.45 (d, J=6.0 Hz, 2H), 2.80-2.76 (m, 2H), 2.51 (t, J=1.8 Hz, 2H), 1.48-1.41 (m, 2H), 1.40-1.30 (m, 2H), 0.89 (t, J=7.2 Hz, 3H); $^{13}$C NMR (100 MHz, DMSO): δ 165.5, 165.5, 143.2, 139.6, 135.3, 132.3, 130.0, 129.4, 128.0, 127.6, 122.4, 51.4, 42.5, 30.3, 20.3, 14.4. [(m+H$^+$)/z=352.25]. ($\lambda_{254}$) purity 98.9%, $t_R$ 12.67 mins.

N-(4-(2-pentylhydrazine-1-carbonyl)benzyl)cinnamide (3d)

2 mmol of 3sm was dissolved in 100 mL ethanol with ultra-sonication aid. To this solution was added 40 mmol of magnesium sulfate and 2 mmol of pentanal. From here the reaction proceeded as described in Series 2 General Procedure to yield 584 mg (80% yield). $^1$H NMR (400 MHz, DMSO): δ 10.0 (s, 1H), 8.7 (t, J=6.0 Hz, 1H), 7.8 (d, J=8.3 Hz, 2H), 7.58 (d, J=6.8 Hz, 2H), 7.49 (d, J=15.8 Hz, 1H), 7.45-7.35 (m, 5H), 6.71 (d, J=15.8 Hz, 1H), 5.06 (s, 1H), 4.45 (d, J=6.0 Hz, 2H), 2.80-2.75 (m, 2H), 2.51 (t, J=1.8 Hz, 2H), 1.47-1.44 (m, 2H), 1.33-1.29 (m, 4H), 0.88 (t, J=7.2 Hz, 3H); 13C NMR (100 MHz, DMSO): δ 165.5, 165.5, 143.2, 139.6, 135.3, 132.3, 130.0, 129.4, 128.0, 127.6, 122.4, 51.7, 42.5, 29.3, 27.8, 22.5, 14.4. [(m+H$^+$)/z=366.25]. ($\lambda_{254}$) purity 97.5%, $t_R$ 13.34 mins.

N-(4-(2-hexylhydrazine-1-carbonyl)benzyl)cinnamamide (3e)

2 mmol of 3sm was dissolved in 100 mL ethanol with ultra-sonication aid. To this solution was added 40 mmol of magnesium sulfate and 2 mmol of hexanal. From here the reaction proceeded as described in Series 2 General Procedure to yield 616 mg (81% yield). H NMR (400 MHz, DMSO): δ 10.00 (s, 1H), 8.71 (t, J=6.0 Hz, 1H), 7.82-7.82 (m, 2H), 7.60-7.58 (m, 2H), 7.55 (d, J=16 Hz, 1H), 7.45-7.36 (m, 5H), 6.73 (d, J=15.6 Hz, 1H), 5.07 (s, 1H), 4.47 (d, J=6.0 Hz, 2H), 2.81-2.76 (m, 2H), 1.49-1.41 (m, 2H), 1.37-1.27 (m, 6H), 0.86 (t, J=6.8 Hz, 3H); $^{13}$C NMR (100 MHz, DMSO): δ 165.6, 165.5, 143.2, 139.6, 135.3, 132.3, 130.0, 129.4, 128.0, 127.6 (d), 122.4, 51.7, 42.5, 31.7, 28.1, 26.8, 22.6, 14.4. [(m+H$^+$)/z=380.33]. ($\lambda_{254}$) purity 95.5%, $t_R$ 13.62 mins.

Example 4

Synthesis of (E)-2-(2-methyl-1H-indol-3-yl)-N-(4-(3-oxo-3-(2-propylhydrazinyl)prop-1-en-1-yl)benzyl)ethan-1-aminium 2,2,2-trifluoroacetate (LL97)

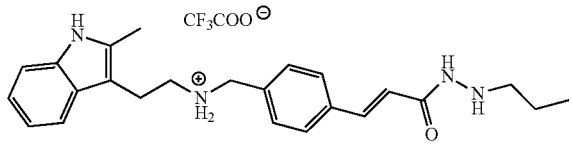 [SMILES: CCCNNC(=O)/C=C/c1ccc(C[NH2+]CCc2c(C)[nH]c3ccccc23)cc1 ; "CF3COO"]

2-(2-methyl-1H-indol-3-yl)ethan-1-amine (365 mg, 2.1 mmol) was dissolved in 30 mL methanol, to this solution was added (E)-3-(4-formylphenyl)acrylic acid (352 mg, 2 mmol), sodium cyanoborohydride (620 mg, 10 mmol) and 2 drops of acetic acid. The mixture was allowed to stir overnight and volatiles were removed under vacuum. The residue was dissolved in 15 mL 1 mol/L NaOH aqueous solution, to which was added 479 mg Boc$_2$O and 2 mL THF. The mixture was stirred overnight and THF condensed under vacuum. The left NaOH aqueous solution was acidification by diluted hydrochloric acid and then was extracted by 20 mL ethyl estate for three times. The organic layer was washed by brine and dried over anhydrous MgSO$_4$. The solvent was evaporated under vacuum and then the residue was dissolved in 30 mL DCM. To this solution was added 770 mg 2-(1H-benzotriazole-1-yl)-1,1,3,3-tetramethyluronium tetrafluoroborate (TBTU) and 0.4 mL trimethylamine. After 30 mins, hydrazinehydrate (200 mg, 4 mM) was added and the mixture was allowed to stir at room temperature overnight. Volatiles were removed under vacuum, the residue was recrystallized by ethyl estate and hexane to yield a white solid. This compound and 116 mg propionaldehyde were dissolved in 50 mL ethanol and reacted for 2 hours. Vacuum evaporation afforded the desired intermediate which was dissolved in 50 mL methanol, to this solution was added 5 mg methyl orange and 620 mg sodium cyanoborohydride. Mixture of methanol and concentrated hydrochloric acid (1:1) was added dropwise until the solution turned and stayed red. 6 hours later, volatiles were removed under vacuum and purified on reverse phase columns eluted with acetonitrile and water to yield pure product. This intermediate was dissolved in 10 mL mixed solution of DCM and TFA (1:1), the solution was stirred at room temperature for 1 hour. The volatiles were evaporated under vacuum and the residue was recrystallized by ethyl ether to afford the end product. $^1$H NMR (400 MHz, DMSO) δ 10.85 (s, 1H), 9.75 (s, 1H), 7.64 (d, J=8.2 Hz, 2H), 7.53 (d, J=8.2 Hz, 2H), 7.50-7.37 (m, 2H), 7.25 (d, J=8.0 Hz, 1H), 7.03-6.99 (m, 1H), 6.97-6.92 (m, 1H), 6.60 (d, J=16 Hz, 1H), 4.27-4.17 (m, 2H), 3.12-2.94 (m, 4H), 2.73-2.64 (m, 2H), 2.32 (d, J=2.3 Hz, 3H), 1.51-1.35 (m, 2H), 0.88 (t, J=7.4 Hz, 2H).

Example 5

Biological Assays

Hek293 Lysate Inhibition Assays.

Hek293 cells were purchased from ATCC and cultured in Dulbecco's modified eagle's medium with glutamax and 10% (v/v) FBS. Cells were plated in 75 cm$^2$ flasks and incubated at 37° C. and 5% CO$_2$ until ~80% confluent. Cells were harvested, washed, and pelleted, lysed before protein concentration was determined using a Tecan M200 spectrophotometer in a BCA assay, and finally stored at −80° C. Upon need, lysate was thawed and diluted to 1 mg/mL of protein concentration with HDAC Buffer. HDAC buffer was comprised of 50 mM Tris HCl with 137 mM NaCl, 2.7 mM, and 1 mM MgCl$_2$. The solution was buffered to a pH of 8 and addition of 1 mg/mL BSA was added. 10 μL of this diluted lysate solution was added in 96-well format black U-bottom plates. Serially diluted inhibitor solution was added and a 2 hour pre incubation occurred at 37° C. 50 μM (final) of Acetylated Lysine-Aminomethyl coumarin-BOC in HDAC buffer solution was added and a second 2 hour incubation occurred at 37° C. 5 mg/mL trypsin, 1 μM trichostatin A solution in HDAC buffer was added to quench the reaction. Fluorescence was read at 360 (ex.)/460 (em.) using a Tecan M200 Pro. Data were normalized to control wells containing no inhibitor. IC$_{50}$'s were determined using GraphPad Prism's built in "log(inhibitor) vs. normalized response—Variable slope" function.

Recombinant HDAC Inhibition Assays.

Recombinant HDACs 1, 2, and 3 (BPS Biosciences) were diluted to a concentration of 1 nM in HDAC buffer. 10 uL of this solution was added in 96-well format to black U-bottom plates. 10 uL of serially diluted inhibitor was added and a 2 hour pre incubation occurred at room temperature. 50 μM (final) of Acetylated Lysine-Aminomethyl coumarin-BOC in HDAC buffer solution was added and a second 2 hour incubation occurred at room temperature. 5 mg/mL trypsin, 1 µM trichostatin A solution in HDAC buffer was added to quench the reaction. Fluorescence was read at 360 (ex.)/460 (em.) using a Tecan M200 Pro. Data were normalized to control wells containing no inhibitor. $IC_{50}$'s were determined using GraphPad Prism's built in "log (inhibitor) vs. normalized response—Variable slope" function.

ESI-LCMS Glucuronidation Assays.

Mixed gender pooled Human Liver Microsomes (HLMs) were purchased from Xenotech, Lot#H0160. A buffer solution containing 100 mM Tris HCl buffered to a pH of 7.5 at 37° C. was used to dilute HLMs to a concentration of 250 µg/mL. To this solution was added 1 µg/mL (final) of alamethicin and 5 mM $MgCl_2$ (final). This solution was rocked gently at 4° C. for 15 minutes to allow pore formation. 180 µL of this solution was added to 10 µL of 5 mM inhibitor+10 µL of 50 mM UDPGA in $H_2O$ or just 10 µL $H_2O$. This solution was gently rocked at 37° C. for 12 hours before being quenched with a 47:50:3 (v/v/v) solution of water, acetonitrile and formic acid. After a 15 minute centrifugation at 15000G in 37° C. conditions, 20 µL of supernatant was directly injected into Thermo LTQ Fleet LCMS.

ESI-LCMS Protocol.

An Accucore RP-MS HPLC Column, 2.6 m particle size, 30×4.6 mm was used throughout these assays. Water and methanol with 0.1% (v/v) formic acid were used as mobile phase. A gradient of 10% methanol 90% water was run isocratically for 2 minutes at 500 L/min. The gradient then changed to 100% methanol over 10 minutes before returning to 10% methanol 90% water over the next three minutes. Capillary temperature was 350° C., with a spray voltage of 5 kV.

Recombinant HDACs 1 and 3 $V_{max}$ Studies.

Recombinant human HDACs 1 and 3 were diluted to a concentration of 0.25 nM (final) using HDAC buffer. 100 µL of enzyme solution was added in 96-well format to black U-bottom plates. 100 µL of inhibitor at various concentrations, diluted in HDAC buffer, was added. A 2 hour room temperature pre-incubation occurred before addition of 20 µL serially diluted Acetylated Lysine-Aminomethyl coumarin-BOC substrate in HDAC buffer. An additional 2 hour room temperature incubation occurred before addition of 20 µL of 5 mg/mL trypsin, 1 µM trichostatin A solution in HDAC buffer to quench the reaction. Fluorescence was read at 360 nm (ex.)/460 nm (em.) using a Tecan M200 Pro. $V_{max}$s and $K_m$s were determined using GraphPad Prism's built in Michaelis-Menten function. Corresponding Lineweaver-burke double reciprocal plots were derived from these values and plotted accordingly.

MV4-11 $EC_{50}$ Analysis.

MV4-11 cells were purchased from ATCC. The cells were grown according to ATCC protocol in Iscove's Modified Deulbecco's Medium with 10% Fetal Bovine Serum. Cells were grown in 37° C. environments with 5% $CO_2$. Cells were plated at 20 k cells/well in 96-well clear U-bottom plates and pre-incubated for 24 hours. Addition of serially diluted inhibitor (in medium) was performed followed by 48 hours of additional incubation. Addition of CellTiter-Blue occurred to a final concentration of 0.125 mg/mL. The mixture was allowed to incubate until sufficient color changed occurred. Cell viability was measured as a function of resorufin intensity using a Tecan M200 Pro spectrophotometer, 560 nm (ex.)/590 nm (em.). Data were normalized to control wells and background was removed. $EC_{50}$'s were determined using GraphPad Prism's built in "log(inhibitor) vs. normalized response—Variable slope" function.

Western Blot Analysis of MV4-11 Cells.

MV4-11 cells were cultured as described above. Cells were plated at 500 k cells/mL×3 mLs in clear, flat bottom 6 well plates. Cells were pre-incubated for 24 hours before addition of inhibitor at various concentrations. The cells were allowed to incubate for 24 additional hours before being harvested, pelleted, and stored at −80° C. overnight. Cell pellets were lysed with RIPA buffer. RIPA buffer is comprised of 50 mM Tris Base, 150 mM NaCl, 5 mM EDTA, 0.1% (v/v) SDS, 0.5% (v/v) Sodium Deoxycholate, and 1% (v/v) Triton-x-100. After lysing, the suspension is ultra-sonicated and centrifuged at 15000 RPM for 15 minute at 4° C. 80 µL of supernatant was mixed with 40 µL of 15:85 (v/v) 3-mercaptoethanol:LDS solution. The mixture was heated at 90° C. for 15 minutes and stored for loading at −20° C. Prior to loading, the solution was flash thawed at 90° C. Lysates were run on Invitrogen NuPAGE 4-12% Bis-Tris 15 well gels at 170V for approximately 60 minutes in MES buffer. Gels were transferred to methylcellulose and ran at 30V for 180 minutes. Primary antibodies, purchased from Santa Cruz Biotechnology, were added in 5% (w/v) milk or 5% (w/v) Bovine Serum Albumin fraction V. The antibody was incubated with cellulose overnight at 4° C. before addition of secondary antibody in 5% (w/v) milk or 5% (w/v) Bovine Serum Albumin. Images were read using a GE ImageQuant LAS 4000. Global lighting adjustments of resulting images were made using Adobe Photoshop CC. Quantification was performed using Image Studio Lite 4.0.

Hek293 $EC_{50}$ Analysis.

Hek293 cells were purchased from ATCC. Cells were grown as described above. Cells were plated at 20 k cells/well in 96-well clear U-bottom plates and pre-incubated for 24 hours. Addition of serially diluted inhibitor (in medium) was performed followed by 48 hours of additional incubation. Addition of CellTiter-Blue occurred to a final concentration of 0.125 mg/mL. The mixture was allowed to incubate until sufficient color changed occurred. Cell viability was measured as a function of resorufin intensity using a Tecan M200 Pro spectrophotometer, 560 nm (ex.)/590 nm (em.).

Human Peripheral Blood Mononuclear Cell Analysis.

Human PBMCs were graciously donated from Dr. Nathan Dolloff s laboratory. Cells were flash thawed from liquid nitrogen using RPMI-1640 media+Glutamax and 15% Fetal Bovine Serum and allowed to incubate overnight at 37° C., 5% $CO_2$. Cells were centrifuged at 1000 RPM for 5 minutes. Pelleted, healthy cells were reseeded at 50 k cells/well and treated immediately with serially diluted inhibitors (diluted in medium). Cells were allowed to incubate with inhibitor or vehicle for 24 hours before addition of 0.125 mg/mL (final) CellTiter-Blue. The mixture was allowed to incubate until sufficient color changed occurred. Cell viability was measured as a function of resorufin intensity using a Tecan M200 Pro spectrophotometer, 560 nm (ex.)/590 nm (em.). Data were normalized to control wells and background was removed.

Using the protocols in Example 4, the following data was generated for representative compounds of the invention:

| Compound | HDAC1 IC50 (nM) | HDAC2 IC50 (nM) | HDAC3 IC50 (nM) | HEK293 Lysate IC50 (nM) |
|---|---|---|---|---|
| 1a |  |  | 156.7 ± 28.55 | 727.3 ± 10.75 |
| 1b |  |  | 1362 ± 197.3 | 1688 ± 38.05 |
| 1c |  |  | 311.7 ± 42.82 | 1691 ± 298.3 |
| 1d |  |  | 1547 ± 429.8 | 4676 ± 909.0 |
| 1e |  |  | 68.85 ± 9.39 | 1307 ± 210.0 |
| 1f |  |  | 903.9 ± 154.3 | 3461 ± 669.0 |
| 1g |  |  | 5001 ± 372.5 | >10,000 |
| 1h |  |  | 1892 ± 227.3 | >10,000 |
| 1i |  |  | 294.5 ± 32.64 | 1440 ± 86.09 |
| 1j |  |  | >10,000 | >10,000 |
| 1k |  |  | 892.0 ± 72.47 | 2844 ± 948.0 |
| 1l | 18.87 ± 2.74 | 65.19 ± 10.41 | 8.56 ± 2.06 | 260.6 ± 8.68 |
| 2a |  |  | 1533 ± 227.5 | >10,000 |
| 2b |  |  | >10,000 | >10,000 |
| 2c |  |  | >10,000 | >10,000 |
| 2d | 13.16 ± 2.01 | 77.59 ± 9.52 | 3.47 ± 0.48 | 155.3 ± 27.64 |
| 2e | 20.20 ± 5.04 | 43.65 ± 33.16 | 18.74 ± 4.3 | 263.6 ± 28.52 |
| 2f |  |  | 69.10 ± 0.52 | 1229 ± 136.5 |
| 2g |  |  | 39.93 ± 0.25 | 1621 ± 196 |
| 2h |  |  | 568.7 ± 84.9 | 2161 ± 895.5 |
| 2i |  |  | 1093 ± 334.4 | >10,000 |
| 2j |  |  | 184.1 ± 74.54 | 550.2 ± 133.9 |
| 2k |  |  | >10,000 | >10,000 |
| 2l |  |  | 187.3 ± 0.6 | 427.1 ± 110.5 |
| 2m |  |  | 84.44 ± 7.22 | 1883 ± 212.4 |
| 3a | 29.49 ± 10.71 | 76.57 ± 9.74 | 19.71 ± 1.41 | 171.1 ± 34.23 |
| 3b | 11.81 ± 4.16 | 95.45 ± 34.15 | 0.95 ± 0.19 | 124.4 ± 14.02 |
| 3c | 60.17 ± 20.97 | 70.03 ± 26.38 | 3.67 ± 2.86 | 494.3 ± 209.6 |
| 3d | 47.36 ± 16.79 | 99.56 ± 17.44 | 32.55 ± 1.15 | 690.7 ± 54.67 |
| 3e | 81.36 ± 11.96 | 139.2 ± 29.9 | 149.8 ± 81.63 | 1718 ± 139.1 |

Example 6

Cancer Assays

Figure 2:
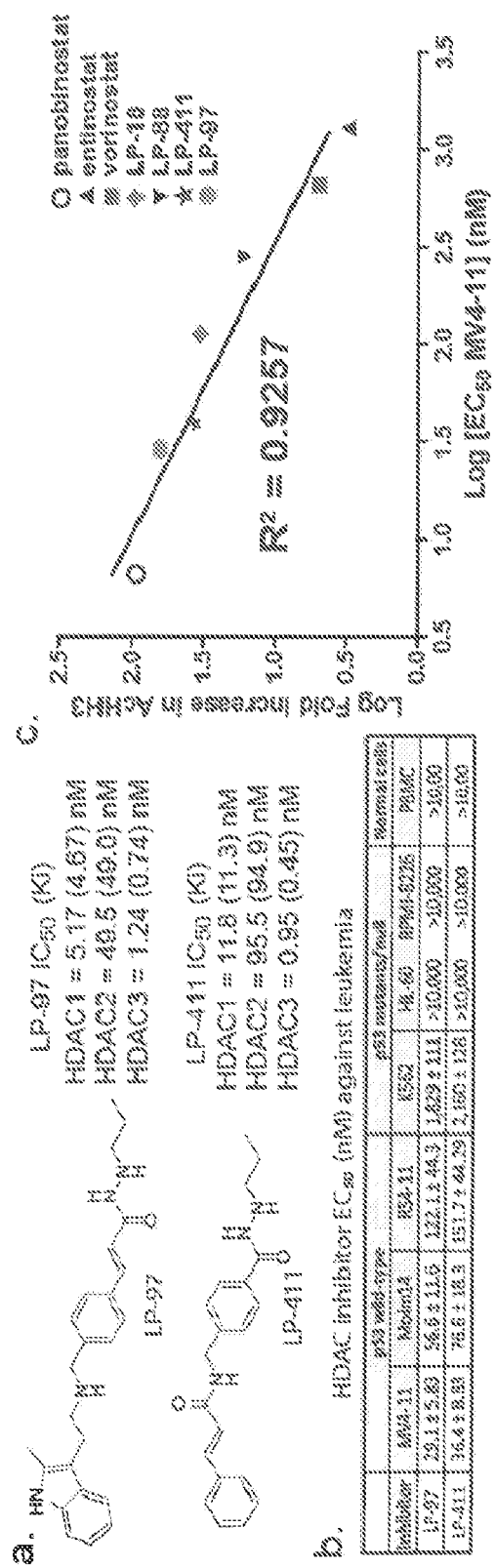
FIG. 2 shows a. allosteric HDAC inhibitors LP-97 and LP-411. b. LP-97 and LP-411 display selective toxicity against wt-p53 versus p53-null and mutants (n=3).[90] c. Efficacy of allosteric inhibitors directly correlates with their ability to induce histone H3 acetylation.

The inventors have developed highly potent class I HDAC inhibitors (FIGS. 1 and 2). These inhibitors, unlike canonical HDAC inhibitors, displayed an allosteric inhibition mechanism (FIG. 1b). They induce selective toxicity against leukemia cells at the low nanoM range, and their ability to induce AML cell death also correlates with their ability to inhibit class I HDACs 1, 2, and 3 and histone acetylation induction (FIG. 2b). In addition, LP-97 and LP-411 displayed better PK parameters compared to the current FDA-approved HDAC inhibitors as described below.

The Allosteric HDAC Inhibitor Induces Selective Toxicity Toward p53 Wild-Type AML Cells.

Allosteric HDAC inhibitors LP-97 and LP-411 are effective in multiple leukemia cell lines with wild-type p53 (wt-p53) status (FIGS. 2a and 2b). The inhibitors are effective at a low nanoM concentration (<100 nM) against multiple AML cell lines. There is also a differential toxicity profile for these inhibitors toward malignant AML cells versus normal blood monocytes (PBMCs) from healthy donors and their p53 status (FIG. 2b). The NIH 60 cell lines panel screen also resulted in a similar trend, that cells containing wt-p53 (A498, ACHN, CAKI-1, SK-MEL-5, UACC-257, UACC-62) are more sensitive than p53-null (HL-60, 786-0, and TK-10) and nuclear p53 nonsense mutant (SN12C). In leukemia, allosteric inhibitors' effective concentration ($EC_{50}$ values) correlates highly with their ability to inhibit HDACs 1, 2, and 3 and induce histone acetylation (FIGS. 2a and 2c). This selective effect is likely due to the difference in p53 function in malignant leukemia cells and normal human PBMCs. For example, normal PBMCs have little HDAC activity and significantly higher acetylated protein levels compared to leukemia cells, which have been suggested to play a role in the effectiveness of HDAC inhibitors against leukemia and multiple myeloma. The p53 status-dependent effect also indicates that the mechanism of action involves p53 function coupled to HDAC activity in leukemia.

Class I Allosteric Inhibitors Induce Lethal Autophagy and Induce Oncogene FLT3/STAT5 Degradation, HDAC6 Depletion, and p53 Down-Regulation.

Figure 3:
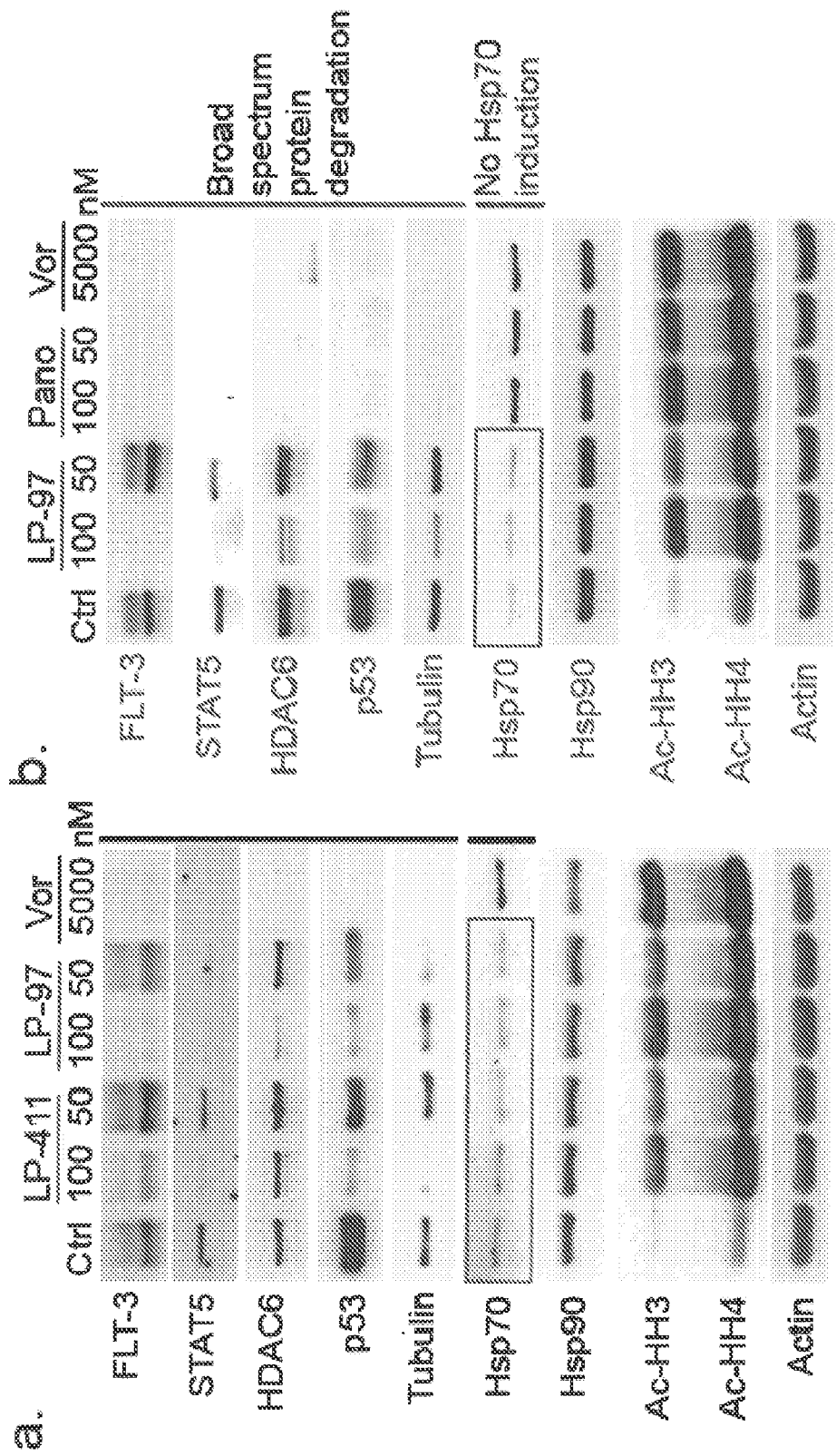
FIG. 3 shows a. LP-411 and LP-97 cause broad-spectrum protein degradation involving multiple signaling pathways including: FLT3/STAT5 (oncogenic signaling), p53 (tumor repressor/oncogene), and HDAC6/tubulin (heat-shock and proteasomal/lysosomal regulation and trafficking). 3b. LP-97 at 100 nM displays similar biological responses compared to panobinostat and vorinostat. No Hsp70 up-regulation was observed for the allosteric HDAC inhibitors (blue box).
Figure 4:
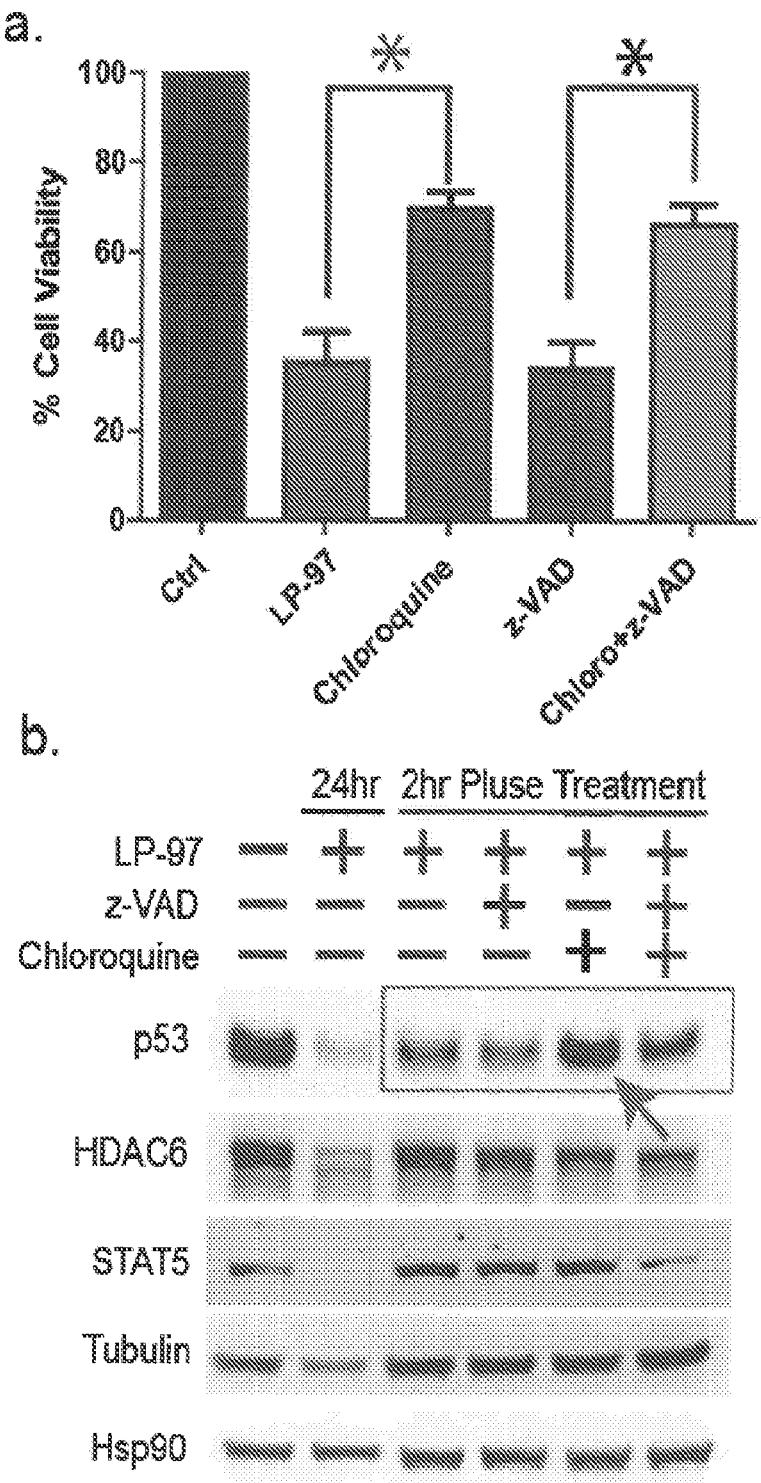
FIG. 4 shows a. 2 hr pulse treatment of LP-97 at 200 nM with either chloroquine or z-VAD followed by a 24 hr incubation (*p<0.001, n=3). b. p53 was depleted with short 2 hr pulse treatment (200 nM, red box) of LP-97. Autophagy inhibitor chloroquine attenuated p53 depletion (red arrow).

The allosteric class I HDAC inhibitors of the invention have high affinity and potency toward HDACs 1, 2, and 3 (FIG. 2a). The inhibitors display selective toxicity against leukemia cells with functional p53 (FIG. 2b). Treatment of AML FLT3-ITD mutant cell line MV4-11 with LP-97 and LP-411 results in degradation of oncogenic proteins FLT3 and STAT5, which are crucial for the survival of leukemia cells. The down-regulation of p53, HDAC6, and tubulin that are key regulators of cell survival, heat-shock function, and proteasome/lysosomal processes was also observed (FIG. 3a). Similar responses were also observed for the less selective inhibitor panobinostat and less potent vorinostat (FIGS. 3a and b). Although apoptosis and caspase-3 cleavage were observed with the allosteric HDAC inhibitor treatment, the inhibitor-induced toxicity is not dependent on apoptosis. The pan-caspase inhibitor z-VAD is incapable of attenuating cell death (FIG. 4a). In the presence of the autophagy inhibitor chloroquine, cell death was rescued, suggesting that allosteric HDAC inhibitors are promoting lethal autophagy in wt-p53 leukemia cells (FIG. 4b). Pulse treatment of MV4-11 cells with the allosteric HDAC inhibitor LP-97 (2 hr treatment followed by removal of the inhibitor and 24 hr incubation) resulted in significant AML cell death and a significant reduction of the p53 level, which is rescued by the co-treatment of chloroquine but not by the pan-caspase inhibitor z-VAD (FIG. 4b). Class I HDAC inhibition triggers p53-dependent autophagy activation through down-regulation of p53, resulting in oncogenic protein FLT3/STAT5 degradation. The same process also causes an increase in lysosomal flux, resulting in HDAC6 and tubulin depletion, which plays a key role in regulating Hsp90 and proteasomal/lysosomal function and protein homeostasis. Studies have shown that cytosolic p53 plays a key role in both activation and inhibition of cellular autophagy. It is interesting to note that an increase in Hsp70 level was not observed for the allosteric class I inhibitor but was observed for vorinostat and panobinostat (FIGS. 3a and b). Hsp70 upregulation has contributed to chemo-resistance in cancer therapeutic development, which suggests that the allosteric HDAC inhibitors could be a more effective and durable therapy compared to the classical HDAC inhibitors.

The Allosteric Inhibitors have More Favorable Bioavailability, Toxicity, and In Vivo PK Properties.

Figure 5:
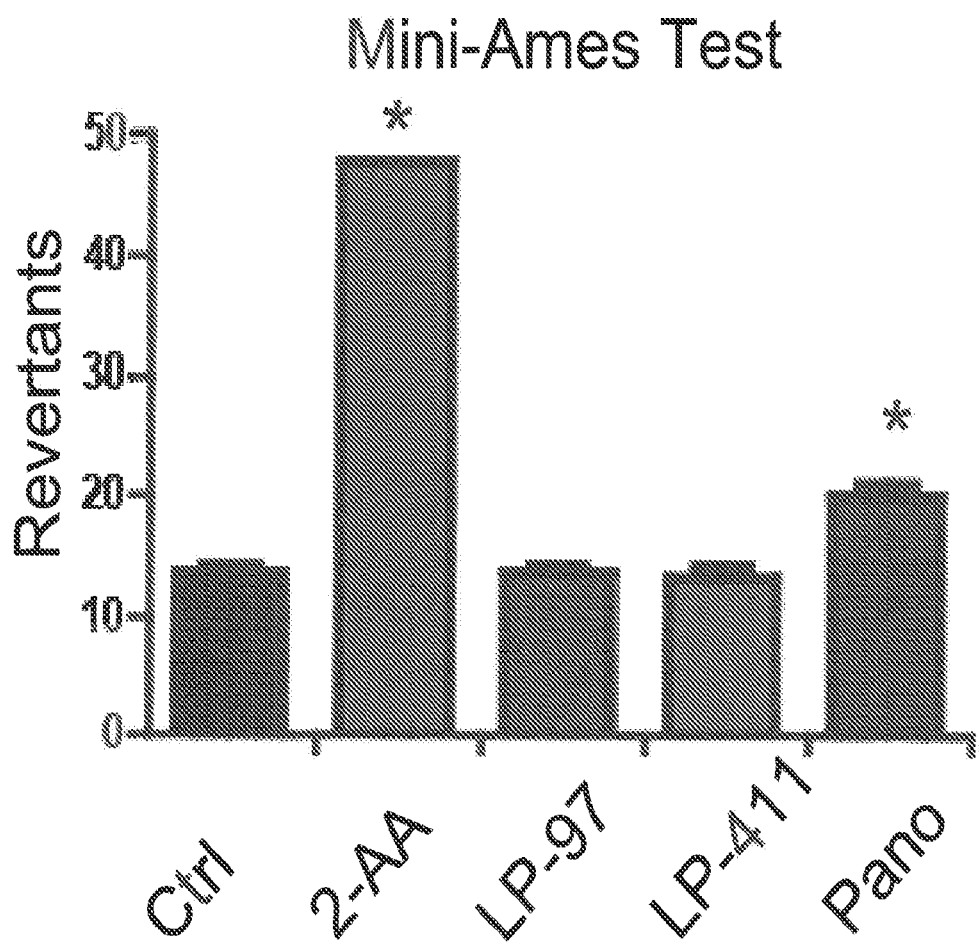
FIG. 5 shows mini-Ames tests (EBPI, Canada) were performed in 96-well format. Mutagen control 2-aminoanthracene (2-AA) and HDAC inhibitor panobinostat (*p<0.01 from ctrl) are Ames positive. Test were ran with TA97a (shown) and TA100 S. typhimurium.
Figure 6:
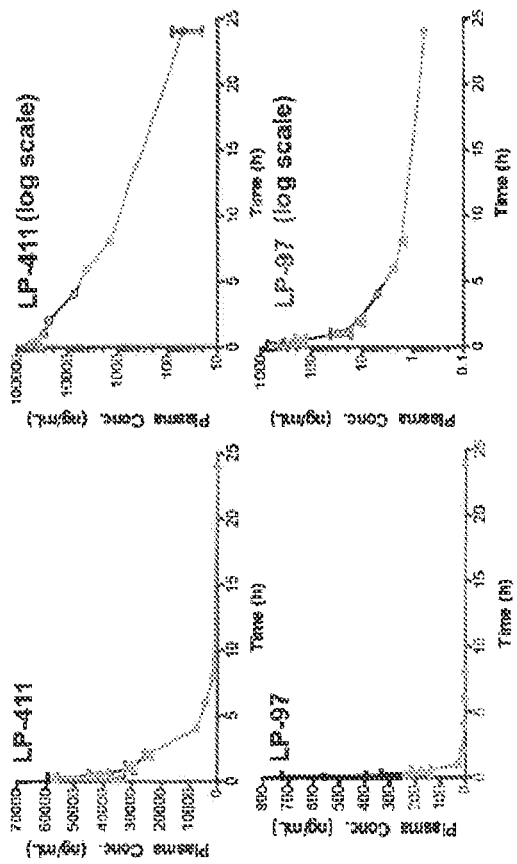
FIG. 6 shows results of an experiment whereby 20 mg/kg of LP-411 and LP-97 were injected via I.P. (n=3), blood was sampled at different time-points after dosing for 24 hr, and the inhibitor plasma concentration was determined via LC-MS/MS. The PK parameters were analyzed. The area under the plasma concentration versus time curve (AUC) is calculated using the linear trapezoidal method. The PK data were fitted to obtain PK parameters using the non-compartmental method.

To be useful as a chemical tool in vivo or as a potential therapy in the clinic, the inhibitors' efficacy and ability to influence targeted biomarkers must be validated in vivo. The chemical agent must also be well tolerated with no overbearing toxicity and with optimized PK properties. Utilizing standard in vitro assays, no appreciable degradation was observed in the artificial gastric and intestinal juice and human serum over 8 hours for LP-97 and LP-411. The candidates are also resistance to glucuronidation by human liver microsomes. The inventors have also demonstrated that hydrazide-based allosteric HDAC inhibitors are not mutagenic comparable to panobinostat and the known mutagen 2-aminoanthracene (FIG. 5). In vivo, the LP-97 and LP-411 have $t_{1/2}$ of 6.07 and 3.34 hours, respectively (FIG. 6), which is significantly longer than vorinostat $t_{1/2}$ of 12 minutes and comparable to panobinostat's $t_{1/2}$ of 2.9 hours in rodent (16 hours in human). LP-97 has similar $C_{max}$ of 559 ng/mL (1.5 microM) at 20 mg/Kg I.P. to vorinostat (501 ng/mL) and about 5 times that of panobinostat (116 ng/mL). Surprisingly, LP-411, unlike other HDAC inhibitors reported, has a $C_{max}$ of 34,433 ng/mL (>100 microM) at 20 mg/kg I.P., which is 50-100 times more than the reported $C_{max}$ of vorinostat, panobinostat, or any HDAC inhibitors reported in mice. These data suggest that both LP-97 and LP-411 are likely to have significantly better bioavailability and half-lives than current HDAC inhibitors on the market, which can be significant factors in therapeutic efficacy and dosing frequency in humans.

Overall, preliminary data demonstrates that the allosteric class I HDAC inhibitors have greater selectivity, better toxicity profile, and significantly better PK parameters than current FDA-approved HDAC inhibitors.

Figure 11:
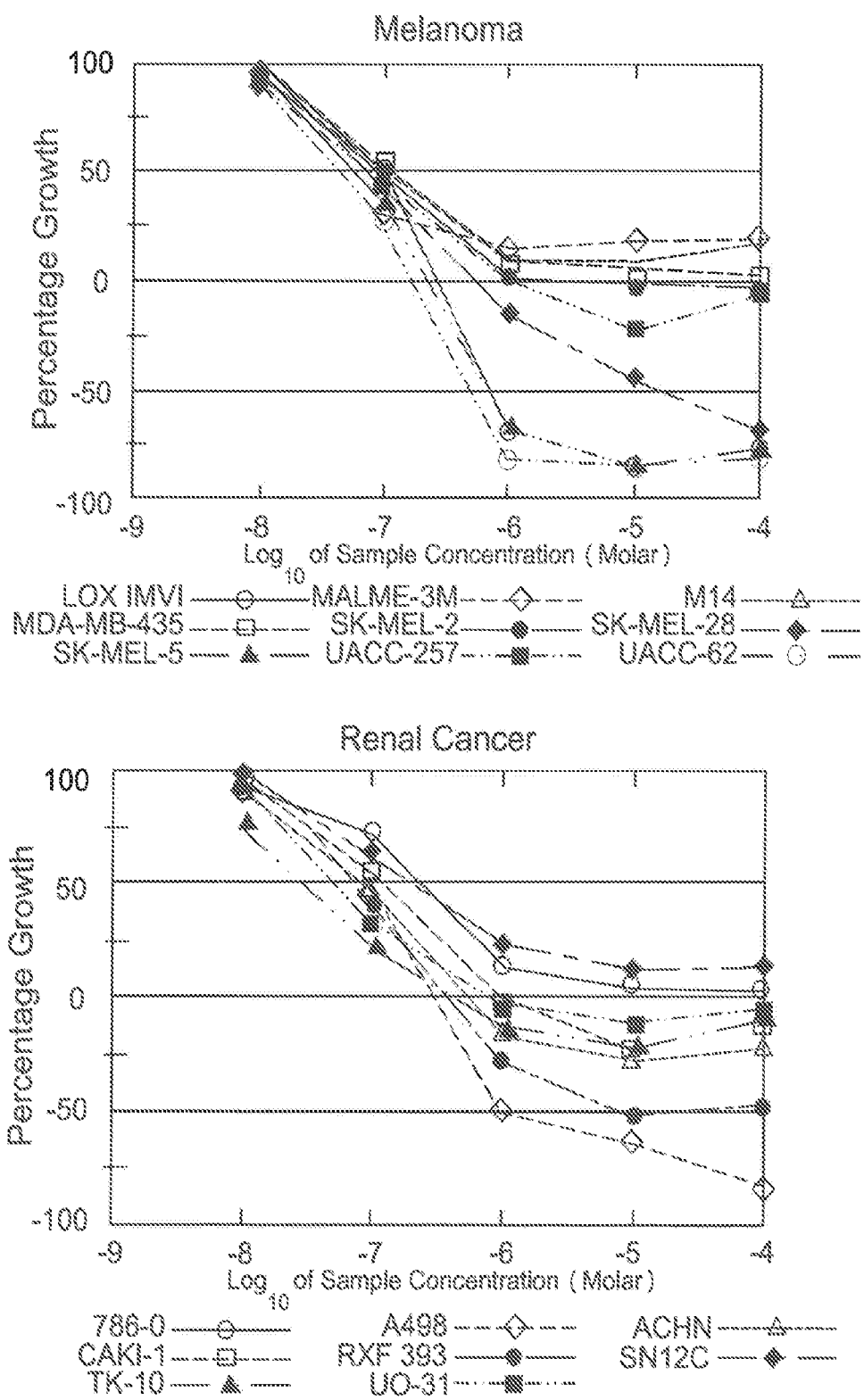
FIG. 11 shows LP-411 efficacy data for melanoma and renal cancer.
Figure 12:
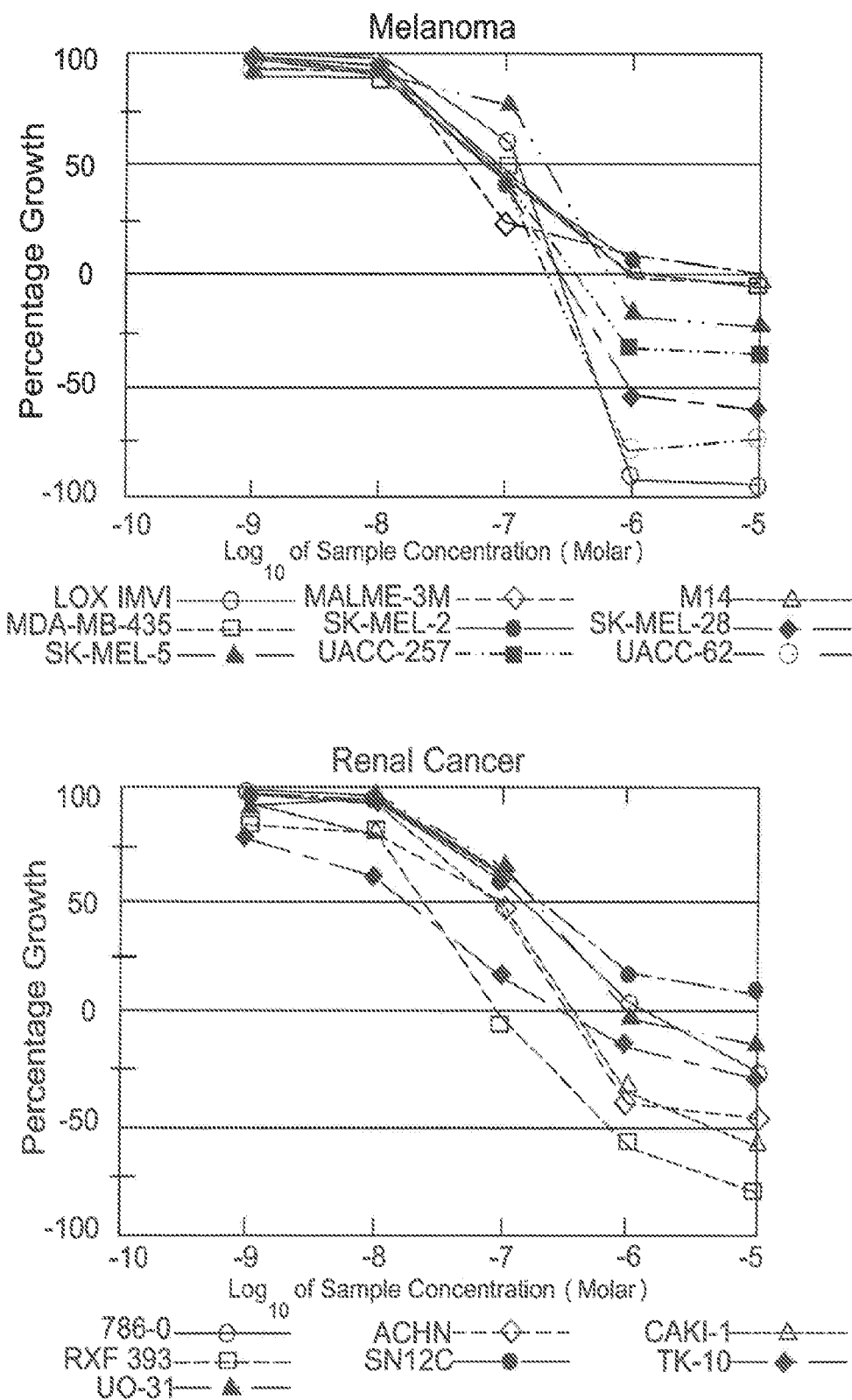
FIG. 12 shows LP-97 efficacy data for melanoma and renal cancer.

Further still, cell line efficacy data suggest that LP-411 (FIG. 11) and LP-97 (FIG. 12) are also effective against both melanoma and renal cancer growth with growth inhibition concentration below 100 nM and total growth inhibition at 1 microM. Percent growth below zero indicates the treatment has selective lethality to the cancer cells.

Example 7

Inflammatory Assays

Macrophage Activation and HDAC3 Inhibition.

Figure 7:
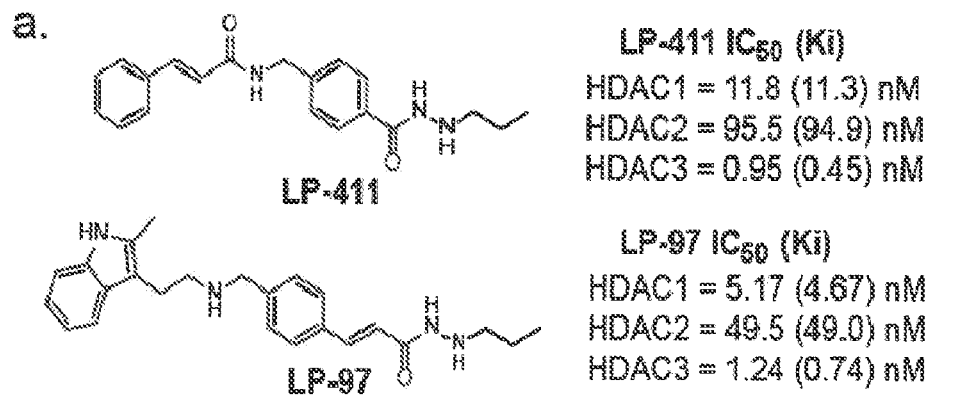
FIG. 7 shows a. low-nanoM to picoM HDAC inhibitors LP-411 and LP-97 targeting class I HDACs. b. The Lineweaver-burk plots of HDAC1 and HDAC3 of LP-411, which indicate a non-competitive allosteric inhibition mechanism. LP-411 has a mixed inhibition profile for HDAC3. c. Allosteric HDAC inhibitors LP-411 and LP-97 have similar potency in vitro comparing to panobinostat. All Treatments are at 100 nM inhibitor concentration.
Figure 7:
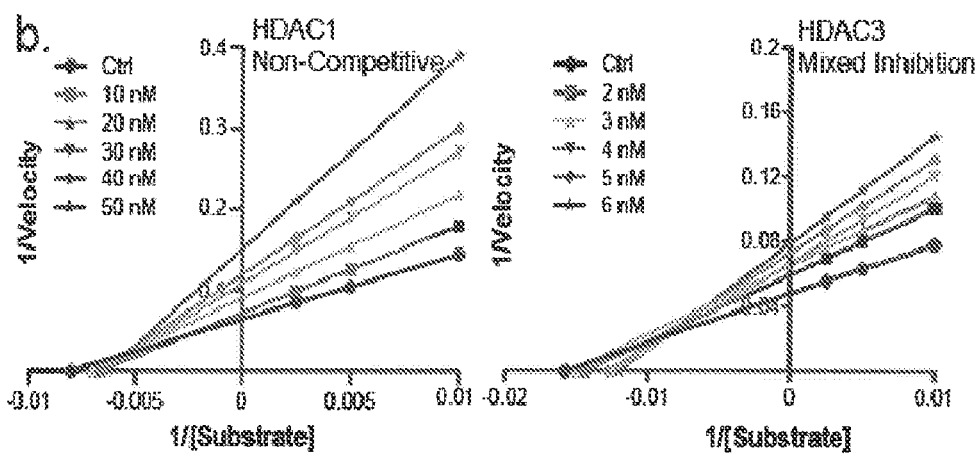
Figure 7:
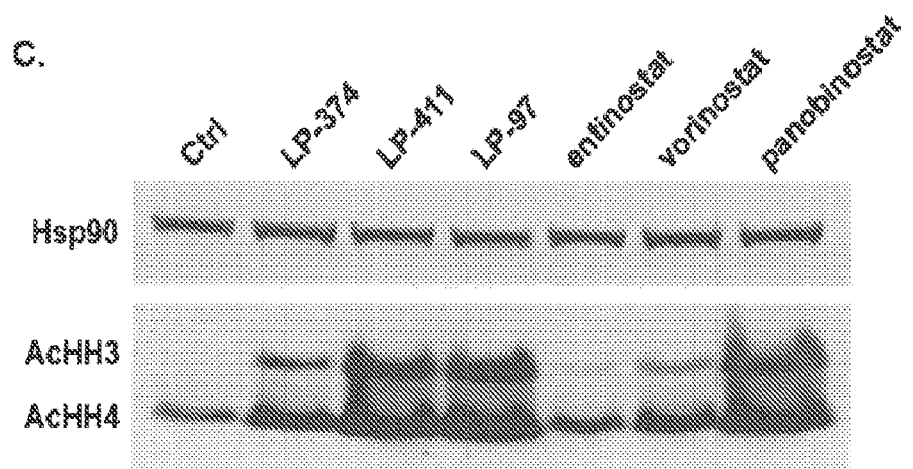
Figure 8:
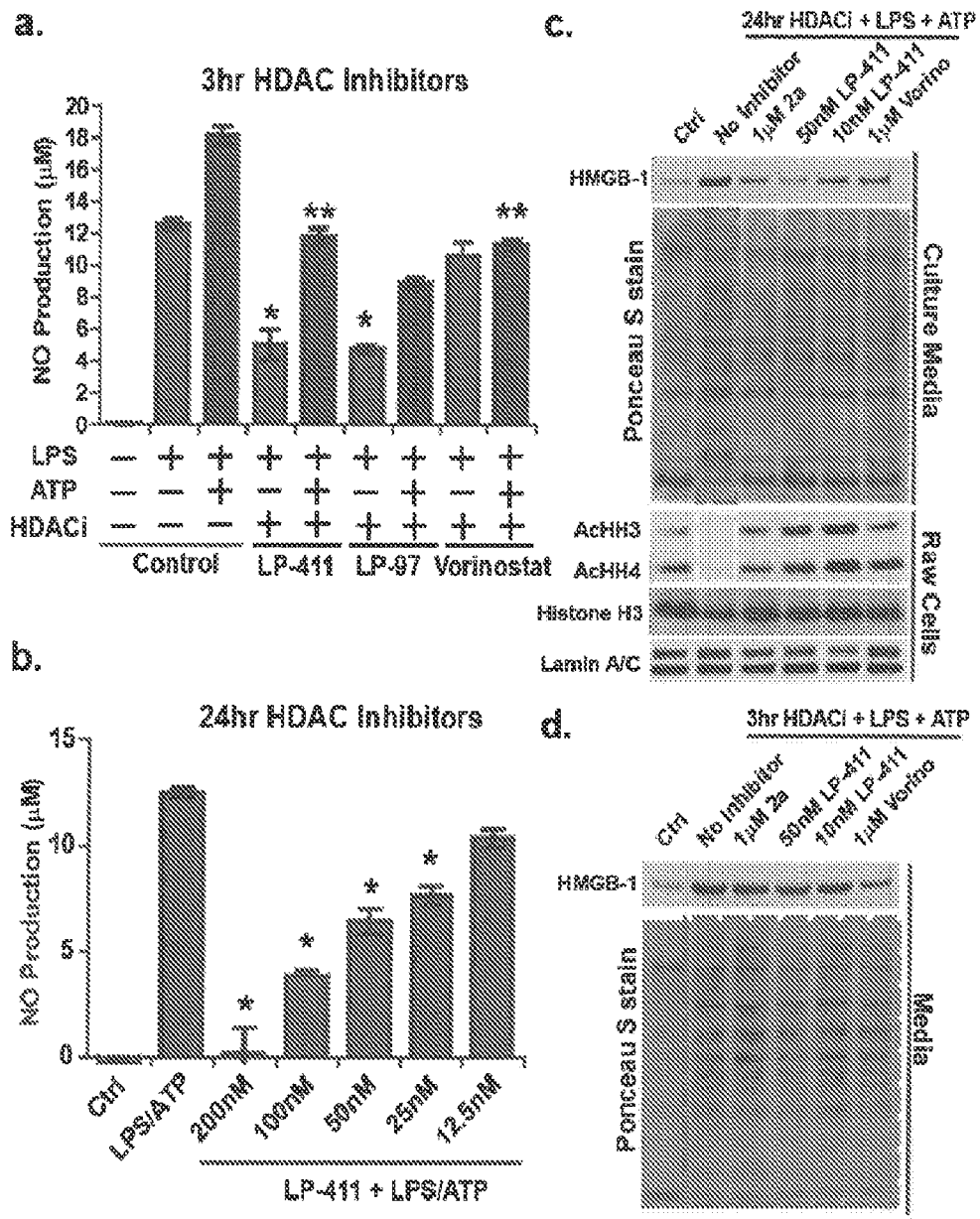
FIG. 8 shows HDAC inhibitors attenuate NO production and HMGB-1 secretion. a. Acute treatments of HDAC inhibitors, LP-411, LP-97, and Vorinostat at 100 nM, only inhibited LPS induced NO production but not ATP driven ones (*p<0.01 **p<0.01 to LPS+ATP and N.S. to LPS only; n=3). b. LP-411 fully inhibited NO production in Raw246.7 macrophage cells at low nanoM range (*p<0.01 to LPS plus ATP activated macrophages, n=3). c. HDAC inhibitors 2a, LP-411, and vorinostat attenuated HMGB-1 secretion by Raw264.7. Total protein ponceau S staining showed a change in the secreted protein profile after LPS plus ATP challenge (red dash boxes), and HDAC inhibitor treated cells maintained a similar secretion profile to the unstimulated control cells. Hypo-acetylation of histone H3 and H4 were also reversed with HDAC inhibitor treatments (yellow dash box). d. Acute HDAC inhibitor treatments do not prevent HMGB-1 secretion and the secreted protein profile.

Innate immunity activation involves two distinct signaling pathways in macrophages: 1) toll-like receptors' recognition of pathogen-associated molecular patterns such as bacterial lipopolysaccharides and 2) assembly of inflammasomes which elicit inflammatory cytokine secretions via a non-conventional secretion pathway or through a caspase-dependent pyroptosis pathway. TLR activation induces the production of inflammatory cytokines, tumour necrosis factor (TNF), interleukin-6, interleukin-8, and nitric oxide independent of inflammasome and cell death. In macrophages, after LPS induction, the addition of ATP results in the activation of inflammasome and the release of interleukin-1b (IL-1b) and HMGB-1 through a distinct secretory pathway or pyroptosis. HDAC activity is mostly associated with epigenetic regulation of inflammatory gene expression. HDAC inhibitors such as SCFAs and hydroxamate HDAC inhibitors have either pro- or anti-inflammatory effect depending on the context and their concentrations. Recent studies have shown that selective inhibition of HDAC3 attenuates NO production and HMGB-1 secretion likely through a NF-☐B-dependent mechanism. However, the current available selective HDAC3 inhibitors are mostly amino-benzamide-based and they are associated with relatively lower in vitro activity, poor in vivo pharmacokinetics, and overbearing toxicity likely associated with the amino-benzamide generated imine metabolites. The inventors recently developed a set of hydrazide-based HDAC inhibitors that is capable of inhibiting HDAC3 and inflammatory responses below 100 nM (FIGS. 7 and 8). The hydrazide moiety is well characterized for its in vivo properties due to its wide usage as the first-generation anti-depression agent targeting monoamine oxidase.

A biphasic response (for short and long treatment periods) from the selective HDAC3 inhibitor was observed. Acute treatment without long pre-incubation of HDAC inhibitors only blocks LPS induced inflammatory NO production in the priming step, but not ATP-associated inflammasome-driven NO secretion, and HMGB-1 secretion was also not attenuated (FIGS. 8a, 8c, and 8d). Complete attenuation of LPS plus ATP activated inflammatory responses required longer pre-incubation of HDAC inhibitor suggesting epigenetic modification is necessary for both NO production and HMGB-1 secretion (FIG. 8b). These results indicate that HDAC3 plays two distinct roles in inflammation responses: one affecting signaling cascades that are rapid and likely regulated through lysine PTMs similar to phosphorylation e.g. NF-☐B p65 nuclear retention time through acetylation/deacetylation, and one affecting inflammasome activation that is controlled epigenetically through repression of pro-inflammatory genes.

The New Allosteric Inhibitors have More Favorable Bioavailability, Toxicity, and In Vivo PK Properties.

Figure 9:
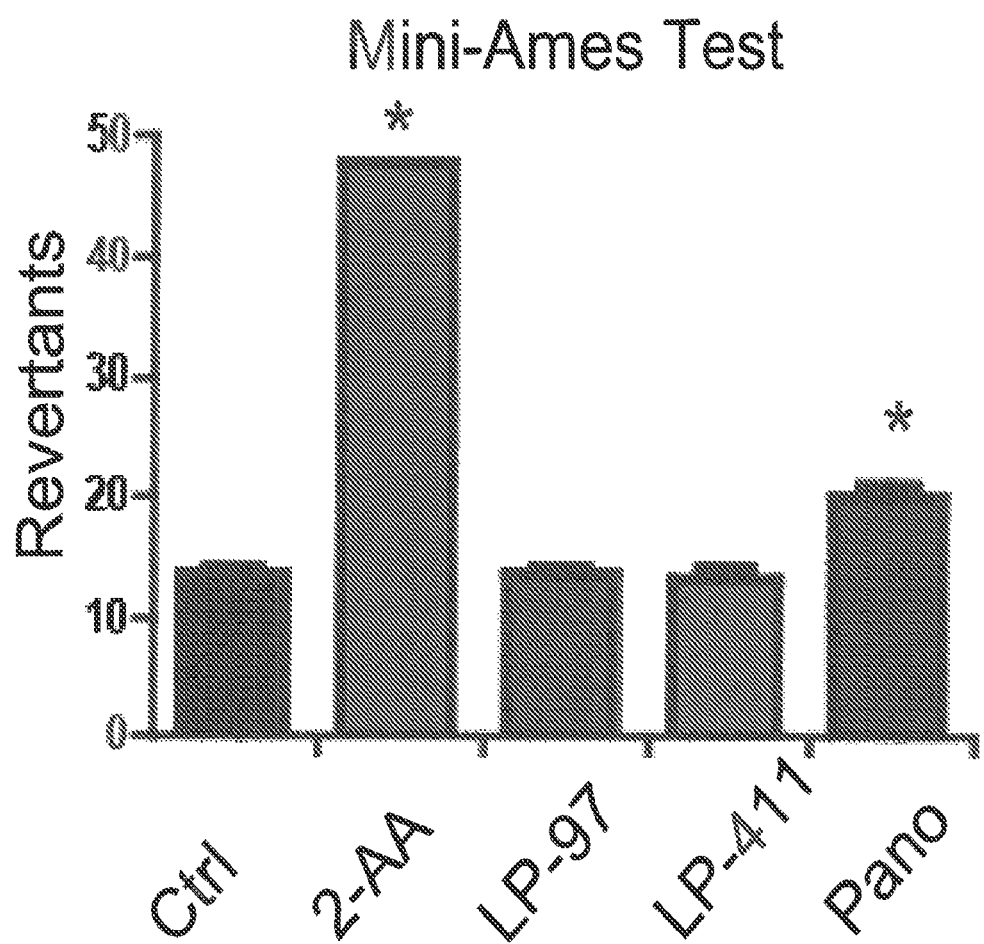
FIG. 9 shows mini-Ames tests (EBPI, Canada) performed in 96-well format. Mutagen control 2-aminoanthracene (2-AA) and HDAC inhibitor panobinostat (*p<0.01 from ctrl) are Ames positive. Tests were run with TA97a (shown) and TA100 *S. typhimurium*.
Figure 10:
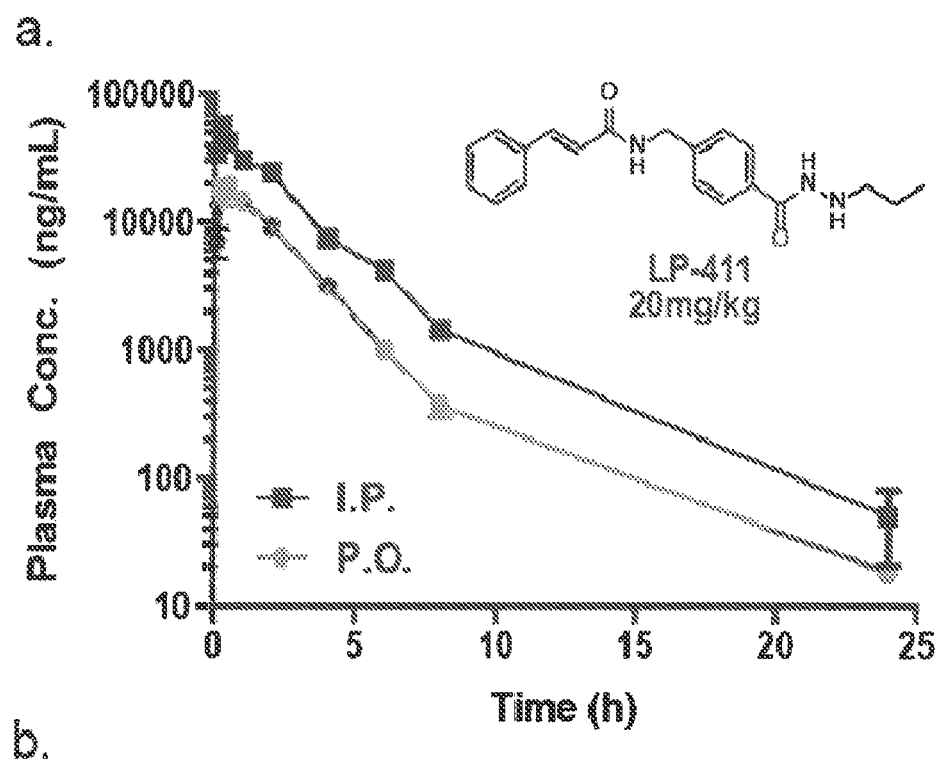
FIG. 10 shows a. LP-411 in vivo PK. a. Semi-log PK profiles for LP-911 at 20 mg/kg (n=3) determined through a 24 hr period. b. PK data for LP-411, LP-97, and FDA approved HDAC inhibitor panobinostat and pracinostat.

To be useful as a chemical agent in vivo or as a potential therapy in the clinic, the inhibitors' efficacy and ability to influence targeted biomarkers must be validated in vivo. The chemical agent must also be well tolerated with no overbearing toxicity and with optimized PK properties. Utilizing standard in vitro assays, no appreciable degradation was observed in the artificial gastric and intestinal juice and human serum over 8 hours for LP-411 and LP-97. The candidates are also resistant to glucuronidation, the most common deactivation step for hydraxamate-based HDAC inhibitor by human liver microsomes. The inventors have also demonstrated that hydrazide-based allosteric HDAC inhibitors are not mutagenic, as compared to panobinostat and the known mutagen 2-aminoanthracene (FIG. 9). In vivo, LP-411 and LP-97 have $t_{1/2}$ of 3.34 and 6.07 hours, respectively (FIGS. 10a and 10b), which is significantly longer than vorinostat $t_{1/2}$ of 12 minutes and comparable to panobinostat's $t_{1/2}$ of 2.9 hours in rodent (16 hours in human). LP-97 has similar $C_{max}$ of 559 ng/mL (1.5 microM)

at 20 mg/Kg I.P. to vorinostat (501 ng/mL) and about 5 times that of panobinostat (116 ng/mL). Surprisingly, LP-411, unlike other HDAC inhibitors reported, has a $C_{max}$ of 19,700 ng/mL (>50 microM) at 20 mg/kg per os, which is 30-40 times more than the reported $C_{max}$ of vorinostat, panobinostat, or any HDAC inhibitors reported in mice. These data suggest that both LP-411 and LP-97 are likely to have significantly better bioavailability and half-lives than current HDAC inhibitors on the market, which are key factors in therapeutic efficacy and dosing frequency in humans. LP-411 is also significantly superior in pharmacokinetic parameters to the best-in-class HDAC inhibitor Pracinostat ($AUC_{inf}$=1,841 ng·h/mL, $C_{max}$=2,632 ng/mL, and $t_{1/2}$=2.4 hr) currently in phase III clinical trial, of which pracinostat recently received FDA Breakthrough Therapy designation (FIG. 7b).

The clinical data suggest that HDAC inhibitors' in vivo efficacy directly correlates with their PK data such as $AUC_{inf}$, $C_{max}$, and time above $IC_{50}$. All these indicate that both LP-411 and LP-97 are likely to have significantly better bioavailability and half-lives than current HDAC inhibitors on the market, which can be important factors in therapeutic efficacy and dosing frequency in humans.

The invention will be further described, without limitation, by the following numbered paragraphs:

1. A compound according to formula (I):

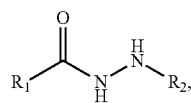

(I)

wherein:
R₁ is—a monocyclic or bicyclic aryl group or a monocyclic or bicyclic heteroaryl group, said aryl and heteroaryl groups optionally substituted independently with alkoxy, O-phenyl, phenyl, —CH₂NHC(O)-phenyl, —CH₂NHC(O)C═C-phenyl or CH═CH-phenyl-CH₂NHCH₂CH₂-1H-indol-3-ylmethyl; or
  a lower alkyl or alkenyl group, optionally substituted with phenyl; and
R₂ is an alkyl or alkenyl group, optionally substituted with —CF₃ or cycloalkyl,
or a pharmaceutically acceptable salt thereof.

2. The compound according to paragraph 1, wherein R₁ is an unsubstituted monocyclic aryl group.
3. The compound according to paragraph 1, wherein R₁ is an unsubstituted monocyclic heteroaryl group.
4. The compound according to paragraph 1, wherein R₁ is an unsubstituted bicyclic aryl group.
5. The compound according to paragraph 1, wherein R₁ is an unsubstituted bicyclic heteroaryl group.
6. The compound according to paragraph 1, wherein R₁ is phenyl substituted with alkoxy, O-phenyl, phenyl, —CH₂NHC(O)-phenyl or —CH₂NHC(O)C═C-phenyl.
7. The compound according to paragraph 1, wherein R₁ is phenyl substituted with —CH₂NHC(O)-phenyl, —CH₂NHC(O)C═C-phenyl or —CH═CH-phenyl-CH₂NHCH₂CH₂-1H-indol-3-ylmethyl.
8. The compound according to paragraph 1, wherein R₁ is phenyl substituted with —CH₂NHC(O)-phenyl.
9. The compound according to paragraph 1, wherein R₁ is methoxybenzyl, benzofuranyl, phenoxybenzyl, pyridinyl, thiophenyl, furanyl, phenyl or naphthyl.
10. The compound according to paragraph 1, wherein R₂ is lower alkyl.
11. The compound according to paragraph 1, wherein R₂ is halo-lower alkyl.
12. The compound according to paragraph 1, wherein R₂ is methyl, ethyl, propyl, butyl, butenyl, isopropyl, propenyl, pentyl, heptyl, octyl, hexyl, decyl, trifluoropropyl, -methylcyclopropyl or -methylcyclobutyl.
13. The compound according to paragraph 1, wherein said compound is:
N'-butyl-4-methoxybenzohydrazide;
N'-butylbenzofuran-2-carbohydrazide;
N'-butyl-4-phenoxybenzohydrazide;
N'-butylnicotinohydrazide;
N'-butyl-[1,1'-biphenyl]-4-carbohydrazide;
N'-butylthiophene-2-carbohydrazide;
N'-butylfuran-2-carbohydrazide;
N'-butyl-3-phenylpropanehydrazide;
N'-butylcinnamohydrazide;
N'-butyl-1-naphthohydrazide;
N'-butyl-2-naphthohydrazide;
N-(4-(2-butylhydrazine-1-carbonyl)benzyl)benzamide;
(E)-N-(4-(2-(but-2-en-1-yl)hydrazine-1-carbonyl)benzyl) benzamide;
N-(4-(2-isopropylhydrazine-1-carbonyl)benzyl)benzamide;
(E)-N-(4-(2-propylidenehydrazine-1-carbonyl)benzyl)benzamide;
N-(4-(2-propylhydrazine-1-carbonyl)benzyl)benzamide;
N-(4-(2-pentylhydrazine-1-carbonyl)benzyl)benzamide;
N-(4-(2-(3,3,3-trifluoropropyl)hydrazine-1-carbonyl)benzyl)benzamide;
N-(4-(2-(cyclopropylmethyl)hydrazine-1-carbonyl)benzyl) benzamide;
N-(4-(2-heptylhydrazine-1-carbonyl)benzyl)benzamide;
N-(4-(2-octylhydrazine-1-carbonyl)benzyl)benzamide;
N-(4-(2-hexylhydrazine-1-carbonyl)benzyl)benzamide;
N-(4-(2-decylhydrazine-1-carbonyl)benzyl)benzamide;
N-(4-(2-ethylhydrazine-1-carbonyl)benzyl)benzamide;
N-(4-(2-(cyclobutylmethyl)hydrazine-1-carbonyl)benzyl) benzamide;
N-(4-(2-ethylhydrazine-1-carbonyl)benzyl)cinnamamide;
N-(4-(2-propylhydrazine-1-carbonyl)benzyl)cinnamamide;
N-(4-(2-butylhydrazine-1-carbonyl)benzyl)cinnamamide;
N-(4-(2-pentylhydrazine-1-carbonyl)benzyl)cinnamamide;
N-(4-(2-hexylhydrazine-1-carbonyl)benzyl)cinnamamide; or
(E)-2-(2-methyl-1H-indol-3-yl)-N-(4-(3-oxo-3-(2-propylhydrazinyl)prop-1-en-1-yl)benzyl)ethan-1-aminium 2,2,2-trifluoroacetate,
or a pharmaceutically acceptable salt thereof.
14. A pharmaceutical composition, comprising a therapeutically effective amount of a compound according to paragraph 1, or a pharmaceutically acceptable salt thereof, and a pharmaceutically acceptable carrier.
15. A method for treating cancer, comprising the step of administering a therapeutically effective amount of a compound according to paragraph 1, or a pharmaceutically acceptable salt thereof, and a pharmaceutically acceptable carrier to a patient in need thereof.
16. The method according to paragraph 15, wherein said cancer is acute myeloid leukemia, melanoma or renal.
17. A method for treating chronic or acute inflammatory diseases, comprising the step of administering a therapeutically effective amount of a compound according to claim 1, or a pharmaceutically acceptable salt thereof, and a pharmaceutically acceptable carrier to a patient in need thereof.

18. A method for treating gene dysregulation, comprising the step of administering a therapeutically effective amount of a compound according to claim 1, or a pharmaceutically acceptable salt thereof, and a pharmaceutically acceptable carrier to a patient in need thereof.

19. The method according to paragraph 18, wherein said gene dysregulation is low expression of frataxin gene due to triplet repeats.

It is to be understood that the invention is not limited to the particular embodiments of the invention described above, as variations of the particular embodiments may be made and still fall within the scope of the appended claims.

What is claimed is:

1. A compound according to formula (I):

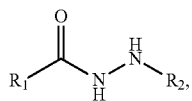

wherein:
R$_1$ is phenyl substituted with —CH$_2$NHC(O)-phenyl, or CH$_2$NHC(O)C=C-phenyl;
and
R$_2$ is (i) an alkyl or alkenyl group, optionally substituted with —CF$_3$ or cycloalkyl, or (ii) halo-lower alkyl,
or a pharmaceutically acceptable salt thereof.

2. The compound according to claim 1, wherein R$_1$ is phenyl substituted with —CH$_2$NHC(O)-phenyl.

3. The compound according to claim 1, wherein R$_2$ is lower alkyl.

4. The compound according to claim 1, wherein R$_2$ is halo-lower alkyl.

5. The compound according to claim 1, wherein R$_2$ is methyl, ethyl, propyl, butyl, butenyl, isopropyl, propenyl, pentyl, heptyl, octyl, hexyl, decyl, trifluoropropyl, -methylcyclopropyl or -methylcyclobutyl.

6. The compound according to claim 1, wherein said compound is:
N-(4-(2-butylhydrazine-1-carbonyl)benzyl)benzamide;
(E)-N-(4-(2-(but-2-en-1-yl)hydrazine-1-carbonyl)benzyl)benzamide;
N-(4-(2-isopropylhydrazine-1-carbonyl)benzyl)benzamide;
(E)-N-(4-(2-propylidenehydrazine-1-carbonyl)benzyl)benzamide;
N-(4-(2-propylhydrazine-1-carbonyl)benzyl)benzamide;
N-(4-(2-pentylhydrazine-1-carbonyl)benzyl)benzamide;
N-(4-(2-(3,3,3-trifluoropropyl)hydrazine-1-carbonyl)benzyl)benzamide;
N-(4-(2-(cyclopropylmethyl)hydrazine-1-carbonyl)benzyl)benzamide;
N-(4-(2-heptylhydrazine-1-carbonyl)benzyl)benzamide;
N-(4-(2-octylhydrazine-1-carbonyl)benzyl)benzamide;
N-(4-(2-hexylhydrazine-1-carbonyl)benzyl)benzamide;
N-(4-(2-decylhydrazine-1-carbonyl)benzyl)benzamide;
N-(4-(2-ethylhydrazine-1-carbonyl)benzyl)benzamide;
N-(4-(2-(cyclobutylmethyl)hydrazine-1-carbonyl)benzyl)benzamide;
N-(4-(2-ethylhydrazine-1-carbonyl)benzyl)cinnamamide;
N-(4-(2-propylhydrazine-1-carbonyl)benzyl)cinnamamide;
N-(4-(2-butylhydrazine-1-carbonyl)benzyl)cinnamamide;
N-(4-(2-pentylhydrazine-1-carbonyl)benzyl)cinnamamide; or
N-(4-(2-hexylhydrazine-1-carbonyl)benzyl)cinnamamide;
or a pharmaceutically acceptable salt thereof.

7. A pharmaceutical composition, comprising a therapeutically effective amount of a compound according to claim 1, or a pharmaceutically acceptable salt thereof, and a pharmaceutically acceptable carrier.

8. A method for treating cancer, comprising the step of administering a therapeutically effective amount of a compound according to claim 1, or a pharmaceutically acceptable salt thereof, and a pharmaceutically acceptable carrier to a patient in need thereof, wherein said cancer is acute myeloid leukemia, melanoma or renal.

9. A pharmaceutical composition, comprising a therapeutically effective amount of a compound according to claim 6, or a pharmaceutically acceptable salt thereof, and a pharmaceutically acceptable carrier.

* * * * *